United States Patent
Schneider et al.

(10) Patent No.: US 12,347,533 B2
(45) Date of Patent: *Jul. 1, 2025

(54) SECURE BIOMETRIC COLLECTION SYSTEM

(71) Applicant: Schneider Advanced Biometric Devices Corp., Sheridan, WY (US)

(72) Inventors: David Lyle Schneider, Hong Kong (CN); Martin Atwood, Canon City, CO (US); Holly Ying Li, New York, NY (US)

(73) Assignee: Schneider Advanced Biometric Devices Corp., Sheridan, WY (US)

( * ) Notice: Subject to any disclaimer, the term of this patent is extended or adjusted under 35 U.S.C. 154(b) by 297 days.

This patent is subject to a terminal disclaimer.

(21) Appl. No.: 17/662,830

(22) Filed: May 10, 2022

(65) Prior Publication Data

US 2022/0270723 A1  Aug. 25, 2022

Related U.S. Application Data

(63) Continuation-in-part of application No. 16/821,990, filed on Mar. 17, 2020, now Pat. No. 11,361,852,
(Continued)

(51) Int. Cl.
| | |
|---|---|
| *H04L 9/40* | (2022.01) |
| *G06F 21/32* | (2013.01) |
| *G06F 21/62* | (2013.01) |
| *G06F 21/64* | (2013.01) |
| *G16H 10/60* | (2018.01) |
| *H04L 9/06* | (2006.01) |

(Continued)

(52) U.S. Cl.
CPC ............ *G16H 10/60* (2018.01); *G06F 21/32* (2013.01); *G06F 21/6245* (2013.01);
(Continued)

(58) Field of Classification Search
CPC ..... G16H 10/60; G06F 21/32; G06F 21/6245; G06F 21/64; H04L 9/06; H04L 9/0866;
(Continued)

(56) References Cited

U.S. PATENT DOCUMENTS 9,977,887 B2 *  5/2018  Bengtsson ............ G06F 3/0227
10,468,129 B2   11/2019  Schneider
(Continued)

FOREIGN PATENT DOCUMENTS

| HK | 1244175 | 3/2018 |
| SE | 1750421-8 | 4/2017 |
| WO | WO2019055147 | 3/2019 |

OTHER PUBLICATIONS

PCT International Search Report in PCT/US18/44823, titled "Collecting Apparatus and Collecting Method", Applicant Schneider, David, Lyle, filed Jan. 8, 2018.
(Continued)

*Primary Examiner* — Ghodrat Jamshidi
(74) *Attorney, Agent, or Firm* — Jonathan Kidney; Intelink Law Group, PC

(57) ABSTRACT

A secure biometric collection (SBC) system for a secure transaction. The system contains inter alia a storage device, an input device receiving user information of the secure transaction, a camera capturing the user's image. A fingerprint scanner scanning the user's fingerprint, a second fingerprint scanner scanning a witness' fingerprint, a camera encoder combining and hashing the user's image into combined data sets being stored in the storage device. A fingerprint encoder processes the fingerprint scans of the user and witness into fingerprint template data sets and stores the fingerprint template data sets in the storage device. A privacy encoder combines and encrypts the combined data sets and fingerprint template data sets into encrypted data sets memorializing the secure transaction. A copy of the secure transaction is produced including encrypted data sets for the user, and the storage device purges of all the user collected data once the copy is produced.

19 Claims, 15 Drawing Sheets

Related U.S. Application Data which is a continuation of application No. PCT/US2018/044823, filed on Aug. 1, 2018, which is a continuation of application No. 15/707,431, filed on Sep. 18, 2017, now Pat. No. 10,468,129.

(60) Provisional application No. 62/395,514, filed on Sep. 16, 2016.

(51) Int. Cl.
*H04L 9/08* (2006.01)
*H04L 9/32* (2006.01)

(52) U.S. Cl.
CPC ............ *G06F 21/64* (2013.01); *H04L 9/06* (2013.01); *H04L 9/0866* (2013.01); *H04L 9/0894* (2013.01); *H04L 9/3231* (2013.01); *H04L 2209/88* (2013.01)

(58) Field of Classification Search
CPC .. H04L 9/0894; H04L 9/3231; H04L 2209/88
See application file for complete search history.

(56) References Cited

U.S. PATENT DOCUMENTS

| | | | | |
|---|---|---|---|---|
| 11,270,309 | B1* | 3/2022 | Ellis | G06Q 20/40145 |
| 2004/0199781 | A1* | 10/2004 | Erickson | G16Z 99/00 |
| | | | | 726/26 |
| 2005/0167484 | A1* | 8/2005 | Sussman | G07F 7/1008 |
| | | | | 235/380 |
| 2010/0094840 | A1* | 4/2010 | Donnelly | G06Q 30/02 |
| | | | | 707/E17.061 |
| 2013/0251214 | A1* | 9/2013 | Chung | G06V 40/19 |
| | | | | 382/116 |
| 2014/0049651 | A1* | 2/2014 | Voth | H04N 21/475 |
| | | | | 348/189 |
| 2014/0074493 | A1 | 3/2014 | Schneider et al. | |
| 2014/0237496 | A1* | 8/2014 | Julian | G06Q 30/02 |
| | | | | 725/13 |
| 2015/0116086 | A1* | 4/2015 | Kim | G06V 40/1335 |
| | | | | 340/5.83 |
| 2015/0181137 | A1* | 6/2015 | Terashima | G01N 21/3151 |
| | | | | 348/162 |
| 2017/0083750 | A1* | 3/2017 | Chin | G06V 40/1306 |
| 2017/0243214 | A1* | 8/2017 | Johnsrud | G06Q 40/03 |
| 2020/0219598 | A1 | 7/2020 | Schneider | |

OTHER PUBLICATIONS

PCT International Preliminary Report on Patentability in PCT/SE2018/050351, titled "Method Performed by a Computer System for Biometric Authentication of Human Beings of a First or a Second Category," Applicant Safe Patient Identification Sweden AB, filed Apr. 4, 2018.

* cited by examiner

SECURE BIOMETRIC COLLECTION SYSTEM

CROSS-REFERENCE TO RELATED APPLICATIONS

This application is a continuation-in-part of United States (U.S.) application Ser. No. 16/821,990, titled "Collecting Apparatus and Method," that was filed on Mar. 17, 2020 that is a continuation of PCT International Application No. PCT/US18/44823, titled "Collecting Apparatus and Collecting Method, filed on Aug. 1, 2018 in the U.S. Receiving Office of the U.S. Patent and Trademark Office, which, in turn, claims priority to U.S. application Ser. No. 15/707,431, titled "Biometric Medical Antifraud and Consent System," filed on Sep. 18, 2017, the disclosures of which are incorporated by reference herein in their entireties.

BACKGROUND

1. Field of the Invention

The present disclosure generally relates to the protection of personally identifiable data, and more particularly, the present disclosure relates to a collecting apparatus and method for reading, encoding, recording and protecting biometric data.

2. Related Art

Modern society has increasingly become a digital based society that increasingly utilizes computer networks to collect, transmit, and process personal data and information from individuals in the society. This personal data and information may be related to, for example, business, employment, private financial and/or medical information and records.

Increasingly, people have been working remotely from their regular places of business, participating in telemedicine doctor's appointments, banking online, and even participated in legal court proceedings remotely. As a result of all these types of activities, there has been a rising challenge to maintain security, privacy, and assure that proper consent is present for these activities.

Unfortunately, this increased digital activity has also increased the activity of hackers who are actively attempting to obtain the secure and private data and information from these activities. These hackers may be motivated by personal, political, nation-state and/or economic objectives. As result, people and business entities are concerned about the safety of their data and information. For example, in the medical industry, patients have a heightened concern about the privacy, accuracy and disclosure of their sensitive health-related information. People are also concerned that their passwords, bank accounts, and credit cards may be vulnerable to these types of hackers.

Current industry trends tend to address these problems with generic security solutions focused on applications, databases, firewalls and activity alarm systems. For example, known approaches for attempting to address these problems may include proprietary encryption of manufactured storage devices installed in servers and workstations to protect against unauthorized disclosure. However, even with these approaches, significant data breaches have still occurred, and will likely continue to occur. This has become a serious public problem that needs to be addressed.

Recently, along with the development of blockchain technologies, industry leaders have started to look into more effective ways to cure the aforementioned problem with this immutable, transparent and decentralized data gatekeeping process. Blockchain is a form of distributed ledger technology (DLT) that allows digitized information such as cryptocurrencies to move freely from one user to another who are located on the same network without the involvement of a central/intermediatory party, such as a central bank. In reality, Blockchain functions as an electronic database, referred to as immutable ledger by some, enables users to keep important information secured and unalterable. Records on a blockchain cannot be changed. Only new data blocks can be created to memorialize any new data input. See https://www.techtarget.com/searchitoperations/tip/Blockchain-An-immutable-ledger-to-replace-the-database. Although blockchain has initially been developed in the financial industry along with transactions of crypto currencies such as Bitcoin or Ethereum, blockchain can also be implemented in many other industries. However, there are still serious lacking of effective blockchain implementations in wide range of industries, such as airport security, police department, medical or public health systems, especially along with security, authentication and antifraud detections.

SUMMARY

Disclosed is a secure biometric collection (SBC) system for collecting and recording data from a user associated with a secure transaction. The SBC system comprises a storage device, input device, camera, fingerprint scanner, camera encoder, fingerprint encoder, and privacy encoder. The input device is configured to receive information from the user related to the secure transaction, the camera is configured to capture an image of the user and store it in the storage device, and the fingerprint scanner is configured to scan a fingerprint of the user and store it in the storage device. The camera encoder is configured to combine and hash the image of the user into combined data sets that are stored in the storage device and the fingerprint encoder is configured to process the fingerprint scan of the user into fingerprint template data sets and store the fingerprint template data sets in the storage device. The privacy encoder is configured to combine and encrypt the combined data sets and fingerprint template data sets from the storage device into encrypted data sets that memorialize the secure transaction. The SBC system is configured to produce a copy of the secure transaction that includes the encrypted data sets for the user and the storage device is configured to be purged of all the data collected from the user including the information from the user and all biometric data that includes the image of the user, fingerprint of the user, combined data sets, fingerprint template data sets, and encrypted data sets once the copy of the secure transaction is produced. The SBC system may be further configured to allow the produced copy of the biometric data of the user into an immutable ledger or a blockchain structure thereby maintaining a history of transactions that are secured, irreversible and decentralized.

Also disclosed is an SBC system that comprises one or more processing units and a computer-readable medium having encoded thereon computer-executable instructions. The computer-executable instructions cause the one or more processing units to: receive information from the user related to the secure transaction with an input device, where the received information from the user is stored in a storage device or an immutable ledger, capture an image of the user with a camera, where the image is stored in the storage device or the immutable ledger, scan a fingerprint of the user with a fingerprint scanner, where the fingerprint of the user is stored in the storage device, combine and hash the image of the user into combined data sets that are stored in the storage device or the immutable ledger, process the fingerprint scan of the user into fingerprint template data sets that are stored in the storage device or the immutable ledger, combine and encrypt the combined data sets and fingerprint template data sets from the storage device into encrypted data sets memorializing the secure transaction, produce a copy of the secure transaction that includes the encrypted data sets for the user, or upload the copy of the secure transaction with the encrypted data sets to the immutable ledger at the user's choice or at an institution's mandate, and purge all the data collected from the user including the information from the user and all biometric data that includes the image of the user, fingerprint of the user, combined data sets, fingerprint template data sets, and encrypted data sets once the copy of the secure transaction is produced.

In an example of operation, the SBC system performs a method that comprises: receiving information from the user related to the secure transaction with an input device; storing the received information from the user in a storage device or an immutable ledger; capturing an image of the user with a camera; storing the image in the storage device or the immutable ledger; scanning a fingerprint of the user with a fingerprint scanner; storing the fingerprint of the user in the storage device or the immutable ledger; combining and hashing the image of the user into combined data sets; storing the combined data sets in the storage device or the immutable ledger; processing the fingerprint scan of the user into fingerprint template data sets; storing the fingerprint template data sets in the storage device or the immutable ledger; combining and encrypting the combined data sets and fingerprint template data sets from the storage device into encrypted data sets memorializing the secure transaction; producing a copy of the secure transaction that includes the encrypted data sets for the user; and uploading the copy of the secure transaction with the encrypted data sets to the immutable ledger at the user's choice before purging all the data collected from the user including the information from the user and all biometric data that includes the image of the user, fingerprint of the user, combined data sets, fingerprint template data sets, and encrypted data sets once the copy of the secure transaction is produced.

Other devices, apparatuses, systems, methods, features, and advantages of the invention will be or will become apparent to one with skill in the art upon examination of the following figures and detailed description. It is intended that all such additional devices, apparatuses, systems, methods, features, and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
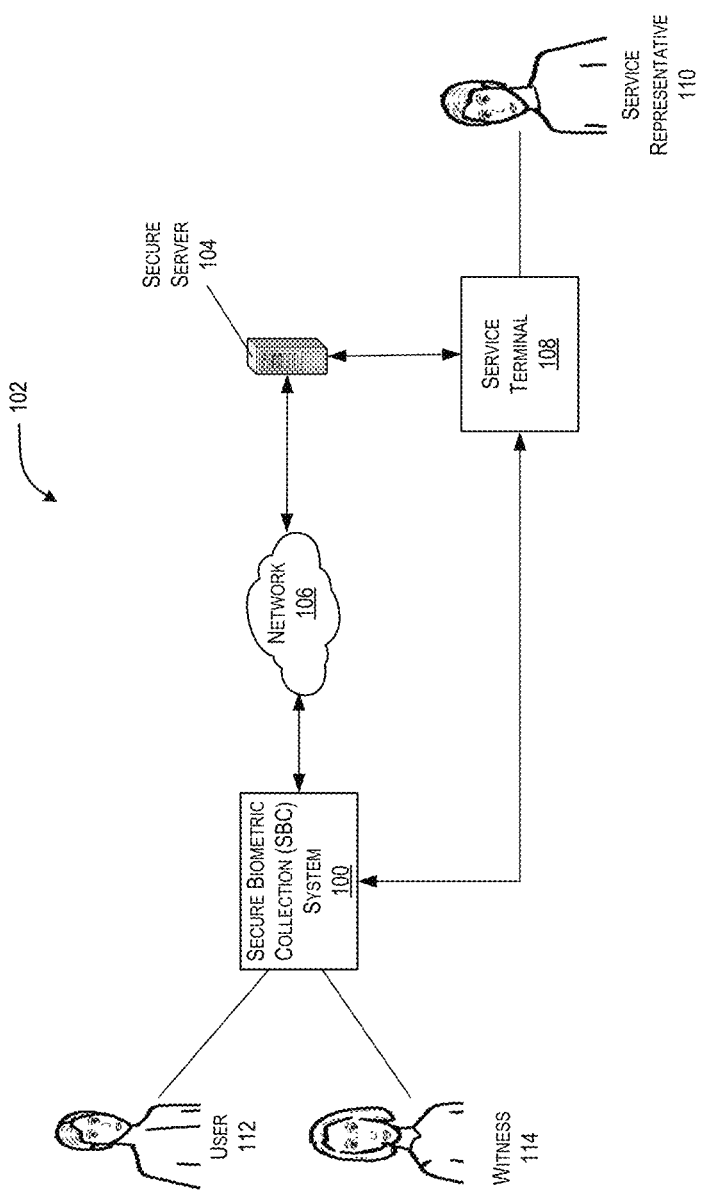
FIG. 1 is a system block diagram of an example of an implementation of a secure biometric collection (SBC) system within a secure network in accordance with the present disclosure.

A secure biometric collection (SBC) system for collecting and recording data from a user associated with a secure transaction is disclosed. The SBC system comprises a storage device, input device, camera, fingerprint scanner, camera encoder, fingerprint encoder, and privacy encoder. The input device is configured to receive information from the user related to the secure transaction, the camera is configured to capture an image of the user and store it in the storage device, and the fingerprint scanner is configured to scan a fingerprint of the user and store it in the storage device. The camera encoder is configured to combine and hash the image of the user into combined data sets that are stored in the storage device and the fingerprint encoder is configured to process the fingerprint scan of the user into fingerprint template data sets and store the fingerprint template data sets in the storage device. The privacy encoder is configured to combine and encrypt the combined data sets and fingerprint template data sets from the storage device into encrypted data sets that memorialize the secure transaction. The SBC system is configured to produce a copy of the secure transaction that includes the encrypted data sets for the user and/or transmit the copy of the secure transaction including the data sets to an immutable ledger at the user's choice; and the storage device is configured to be purged of all the data collected from the user including the information from the user and all biometric data that includes the image of the user, fingerprint of the user, combined data sets, fingerprint template data sets, and encrypted data sets once the copy of the secure transaction is produced and/or transmitted to the immutable ledger.

Also disclosed is an SBC system that comprises one or more processing units and a computer-readable medium having encoded thereon computer-executable instructions. The computer-executable instructions cause the one or more processing units to: receive information from the user related to the secure transaction with an input device, where the received information from the user is stored in a storage device, capture an image of the user with a camera, where the image is stored in the storage device, scan a fingerprint of the user with a fingerprint scanner, where the fingerprint of the user is stored in the storage device, combine and hash the image of the user into combined data sets that are stored in the storage device, process the fingerprint scan of the user into fingerprint template data sets that are stored in the storage device, combine and encrypt the combined data sets and fingerprint template data sets from the storage device into encrypted data sets memorializing the secure transaction, produce a copy of the secure transaction that includes the encrypted data sets for the user, transmit the copy of the secure transaction including the encrypted data sets to an immutable ledger at user's choice and purge all the data collected from the user including the information from the user and all biometric data that includes the image of the user, fingerprint of the user, combined data sets, fingerprint template data sets, and encrypted data sets once the copy of the secure transaction is produced and/or transmitted.

In an example of operation, the SBC system performs a method that comprises: receiving information from the user related to the secure transaction with an input device; storing the received information from the user in a storage device; capturing an image of the user with a camera; storing the image in the storage device; scanning a fingerprint of the user with a fingerprint scanner; storing the fingerprint of the user in the storage device; combining and hashing the image of the user into combined data sets; storing the combined data sets in the storage device; processing the fingerprint scan of the user into fingerprint template data sets; storing the fingerprint template data sets in the storage device; combining and encrypting the combined data sets and fingerprint template data sets from the storage device into encrypted data sets memorializing the secure transaction; producing a copy of the secure transaction that includes the encrypted data sets for the user; transmitting the secure transaction including the encrypted data sets to an immutable ledger at user's choice; and purging all the data collected from the user including the information from the user and all biometric data that includes the image of the user, fingerprint of the user, combined data sets, fingerprint template data sets, and encrypted data sets once the copy of the secure transaction is produced and/or transmitted.

Turning to FIG. 1, a system block diagram of an example of an implementation of a secure biometric collection (SBC) system 100 within a secure network 102 is shown in accordance with the present disclosure. The secure network 102 may include a secure server 104 that communicates with the SBC system 100 via a network 106. The network 106 may include one or more network such as, for example, an Ethernet network, wireless network, the Internet, a distributed blockchain network or other type of communications network. In this example, the service server 104 may include one or more servers utilized by a business or government entity to communicate and control the SBC system 100. The secure server 104 may also communicate with a service terminal 108 that is utilized by the business or government entity to communicate with the SBC system 100 via the secure server 104 and network 106. The service terminal 108 may be a computer device, such as a desktop personal computer, laptop computer, or other computer device utilized by a service representative 110 that works for business or government entity. The secure network 102 can also be designed as a decentralized blockchain structure.

In this example, the secure network 102 may be secure health network and the business entity may be a health provider that utilizes the SBC system 100 to obtain health related information from a user 112. The user 112 may be a person seeking medical care that expects his/her personal information to be kept private. In addition to the user 112, a witness 114 may be present when the user 112 interfaces with the SBC system 100. As an example, the witness 114 may be a parent of the user 112 if the user 112 is underage. In this example, the service representative 110 may be health provider employee that assists the user 112 in processing his/her health care needs. In one example, the SBC system 100 may be a standalone kiosk in a medical facility. Alternatively, the SBC system 100 and the service terminal 108 may be the same system that is physically located near the service representative 110. In this example, combined SBC system 100 and service terminal 108 may be located at a check-in location in the medical facility in front of the service representative where the user 112, and optionally the witness 114, approach the service representative 110 and input the user's 112 information at the SBC system 100 in front of the service representative 110 where the service representative 110 also interfaces directly with the SBC system 100.

In another example, the secure network 102 may be secure government network and the government entity utilizes the SBC system 100 to obtain sensitive government related information from a user 112. In this example, the government entity may be a government taxing authority, courthouse, central bank or other government related facility.

In yet another example, the secure network 102 may be secure government related network and the business entity utilizes the SBC system 100 to obtain sensitive government related information from a user 112. In this example, the business entity may be a defense contractor or a business the performs services for a government entity.

In still another example, the secure network 102 may be a business-related network and business entity utilizes the SBC system 100 as a point-of-sale device. In this example, the user 112 may be a buyer, the SBC system 100 may be combined with the service terminal 108 as a point-of-sale device, and the service representative 110 may be a sales representative of the business entity.

As an example of the business entity being a health provider, the SBC system 100 may be a kiosk (such as, for example SBC system 400) within the facility of the health provider. The user 112 may then approach and activate the SBC system 100 to receive medical services. The SBC system 100 would then prompt the user 112 to input the identify and personal information related to the identity of the user 112 and the requested medical services. For example, is the user 112 requesting to receive medical services for a previously booked medical appointment or walk-in medical services. The user 112 would input this information and any related user data into the SBC system 100 which would be related to a private and secure transaction with the medical provider that may include financial and private medical information about the user 112. This information would be received by SBC system 100 and stored in a storage device. The SBC system 100 may then capture (i.e., take) one or more pictures and/or video of the user 112 with one or more cameras of the SBC system 100. The captured images or videos would then be stored in the storage device. The SBC system 100 would then prompt the user 112 for biometric data such as one or more fingerprints from the user 112 with a fingerprint scanner. The user 112 would then scan his/her fingerprint, or fingerprints, with the fingerprint scanner and the SBC system 100 would store the fingerprint(s) into the storage device. The SBC system 100 would then combine and hash the image (s) of the user into combined data sets and store the combined data sets into the storage device. The SBC system 100 would then process the fingerprint scan of the user into fingerprint template data sets and then store the fingerprint template data sets into the storage device. The SBC system 100 would then combine and encrypt the combined data sets and fingerprint template data sets from the storage device into encrypted data sets memorializing the secure transaction, or transmit the secure transaction and including the encrypted data set to an immutable ledger, and produce a copy of the secure transaction that includes the encrypted data sets for the user 112. The SBC system 100 would then purge all the data collected from the user including the information from the user and all biometric data that includes the image of the user, fingerprint of the user, combined data sets, fingerprint template data sets, and encrypted data sets once the copy of the secure transaction is produced and/or transmitted to the immutable ledger.

In this example, to increase the level of security, the SBC system 100 may require that a second person to authenticate the information provided by the user 112. The second person may be the witness 114 or the service representative 110.

As an example, the user 112 may be a patient that is requiring medical services and the SBC system may collect the information from the user 112 and then present an agreement document for the user 112 to read before services are rendered by the health provider. The agreement may be displayed on display device on the SBC system 100 for the user 112 to read. The SBC system 100 then would prompt the user 112 to accept or decline the agreement document. If the user 112 does not accept the agreement document, the SBC system 100 then ends the session with the user 112 and resets for another user. If, instead, the user 112 does accept the agreement document, the SBC system prompts the user 112 to be photographed and/or video recorded. This prompt may be timed by a first predetermined time (for example, three to five seconds) for the user 112 to prepare to be photographed and/or video recorded by the camera. Once photographed and/or recorded, the SBC system 100 will prompt the user 112 to provide one or more fingerprints via the fingerprint scanner of the SBC system 100. Once the user 112 provides the fingerprint(s), the SBC system 100 may prompt the second person to also provide a fingerprint via the same or another fingerprint scanner. In this situation, the second person may be the witness 114 that is proximate to the user 112 to confirm the acceptance of agreement document by the user 112 or the service representative 110 that may be proximate or remote from the user 112. In the situation where the SBC system 100 is a kiosk (combining the SBC system 100 and service terminal 108) that is close to the service representative 110, the service representative 110 may provide the fingerprint scan while personally viewing and being personally close to the user 112. In the situation where the SBC system 100 is a kiosk that is remote from the service terminal 108 and service representative 110, the service terminal 108 may include a display that shows live video of the user 112 at the SBC system 100, where the video is recorded by a camera of the SBC system 100. In this situation, the service representative 110 may provide a fingerprint to the SBC system 100 via a fingerprint scanner on the service terminal that scans the fingerprint of the remote service representative 110 and transmits the scanned fingerprint of the service representative 110 to the SBC system 100 via the service terminal 108, secure server 104, and network 106.

In these examples, the SBC system 100 may time how long it takes for the second person to provide the fingerprint of the second person to ensure that it is approximately contemporaneous and provided as soon as possible after the user 112 provided the scanned fingerprint. As such, the SBC system 100 may require that the second person's fingerprint is scanned within a second predetermine time, for example about 1000 ms, after the user's 112 fingerprint is scanned. The SBC system 100 determines if the second person's fingerprint was scanned within the second predetermine time by timestamping the user's 112 scanned fingerprint and the timestamping the second person's scanned fingerprint. If the difference between the first timestamp and the second timestamp is within the second predetermined time, the SBC system 100 will accept the second person's fingerprint. If not, the SBC system 100 may require that the user 112 and second person repeat the process of scanning their respective fingerprints until they do it within the second predetermined time.

Once the SBC system 100 accepts that both the user's 112 and the second person's fingerprints were provided within the second predetermined time, the SBC system 100 would then combine and hash the image(s) of the user into combined data sets and store the combined data sets into the storage device. The SBC system 100 would then process the fingerprint scans of the user 112 and second person into fingerprint template data sets and then store the fingerprint template data sets into the storage device. The SBC system 100 would then combine and encrypt the combined data sets and fingerprint template data sets from the storage device into encrypted data sets memorializing the secure transaction, produce a copy of the secure transaction that includes the encrypted data sets for the user 112 and/or transmit the copy of the secure transaction to an immutable ledger located in the same network. The SBC system 100 would then purge all the data collected from the user including the information from the user and all biometric data that includes the image of the user, fingerprint of the user, fingerprint of the second person, combined data sets, fingerprint template data sets, and encrypted data sets once the copy of the secure transaction is produced or being transmitted to the immutable ledger.

In all the above examples, the secure network 102 and SBC system 100 may be powered by high-performance computers (HPCs) to carry out the transmission to an immutable ledger or blockchain step at a user's choice. However, if a user prefers to keep copies the secure transaction to be stored at a traditional storage unit or network due to cost concerns as the HPCs are very costly due to the sophisticated Graphic Processing Units (GPUs) and Central Processing Units (CPUs), the HPCs can be introduced at a later stage when cost is not an issue.

Figure 2:
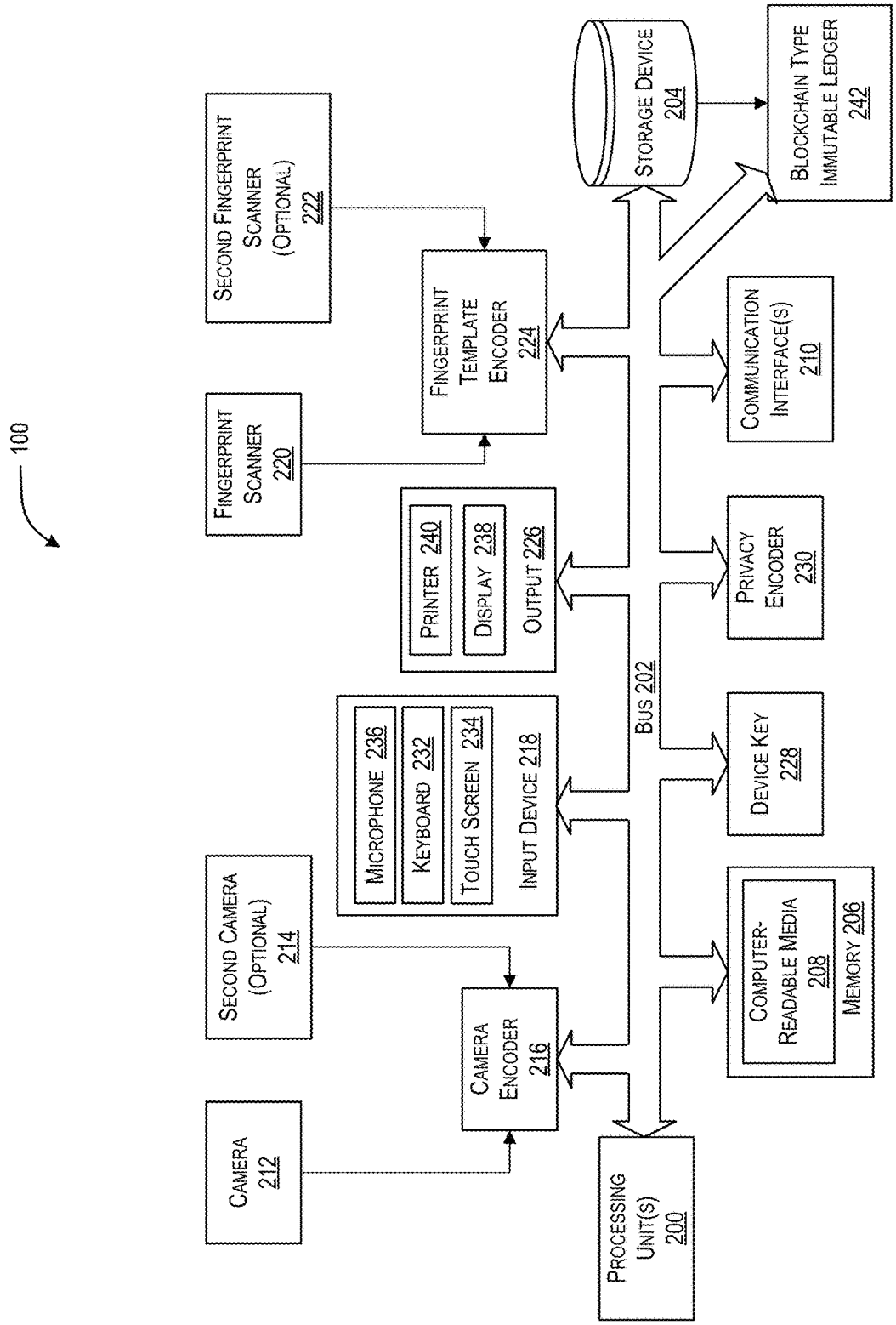
FIG. 2 is a system block diagram of an example of an implementation of the SBC system in accordance with the present disclosure.

In FIG. 2, a system block diagram of an example of an implementation of the SBC system 100 is shown in accordance with the present disclosure. The SBC system 100 one or more processing units 200, a system bus 202, storage device 204, memory 206, computer-readable media 208, one or more communication interfaces 210, first camera 212, optional second camera 214, camera encoder 216, input device 218, first fingerprint scanner 220, optional second fingerprint scanner 222, fingerprint template encoder 224, output device 226, device key 228, and privacy encoder 230. In this example, the input device 218 may include keyboard 232, touch screen 234, and/or a microphone 236. The output device 226 may include a video display 238 and/or a printer 240.

In this example, the one or more processing units 200, storage device, memory 206, one or more communication interfaces 210, camera encoder 216, input device 218, output device 226, fingerprint template encoder 224, device key 228, and privacy encoder 230 are in signal communication with system bus 202 and potentially each other. The camera encoder 216 is also in signal communication with the camera 212 and optional second camera 214 and the fingerprint encoder 224 is also in signal communication with the fingerprint scanner 220 and optional second fingerprint scanner 222. In this example, the one or more processing units 200 may be one or more processors as described in relation to FIG. 3. The storage device 204 may be a temporary memory device that stores information from the input device 218, one or more communication interfaces 210, camera encoder 216, fingerprint template encoder 224, memory 206, one or more processing units 200, device key 228, and privacy encoder 230. The memory 206 may be a part of the storage device or storage that is separate from storage device. The memory 206 is configured to operate with the one or more processing units 200 and includes the computer-readable media 208 that stores computer-executable instructions that cause the one or more processing units 200 to perform the functions and methods of the SBC system 100.

In this example, the camera 212 may be a camera capable of capturing photographic images and/or video of the user 112 in the visible radiation spectrum. If the optional second camera 214 is present, the optional second camera 214 may be camera capable of capturing photographic images and/or video of the user 112 in the invisible radiation spectrum including ultraviolet spectrum radiation, near-infrared spectrum radiation, or far-infrared spectrum radiation.

Moreover, in this example the fingerprint scanner 220 is located on the SBC system 100 and is configured to scan one or more fingerprints of the user 112. The fingerprint scanner 220 may be a signal scanner that is configured to scan the fingerprint of a single finger of the user 112 or one or more fingerprint scanner that are configured to scan multiple fingers of the user 112. In this example, the user 112 and witness 114 may utilize a single fingerprint scanner 220 to scan the fingerprints of the both the user 112 and witness 114 (acting as a second person as described previously). Alternatively, the SBC system 100 may include the optional second fingerprint scanner 222 to scan the fingerprint of the second person (such as the witness 114 or service representative 110. If the optional second fingerprint scanner 222 is configured to scan the fingerprint of a second person that is either the witness 114 or a proximately located service representative 110, the optional second fingerprint scanner 222 may be part of the SBC system 100. If, instead, the optional second fingerprint scanner 222 is configured to scan the fingerprint of a second person that is a remotely located service representative 110 (e.g., the service representative 110 may be located in another area of the same building, another town or city, another state, or even another country), optional second fingerprint scanner 222 would be located remotely at the service terminal 108 of the service representative 110. In this example, the fingerprint of the service representative would be scanned at the optional second fingerprint scanner 222 and transmitted to the fingerprint template encoder 224 via the service terminal 108, secure server 104, and network 106.

Furthermore, in this example, the input information from the user 112, photographic/video of the user 112, scanned fingerprints of the user 112 and/or witness 114 or service representative 110 is initially unprotected data. The camera encoder 216 and fingerprint template encoder 224 are hardware components and/or software modules that are configured to encode this unprotected data into encoded data that is then stored in the storage device 204. This encoded data may then be further encoded by the privacy encoder 230 utilizing the device key 228. The device key 228 is a private encryption key that is only known to the SBC system 100 and may be implemented, for example, by a privacy encoder chip. The SBC system 100 can also be designed with HPCs that will enable the transactions and its encryption keys being recorded on an immutable ledger such as a blockchain instead of, or in combination with, storage device 242.

It is appreciated by those skilled in the art that the circuits, components, modules, and/or devices of, or associated with, the SBC system 100 are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical, such as, for example, conductive wires, electromagnetic wave guides, cables, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying digital formats without passing through a direct electromagnetic connection.

Figure 3:
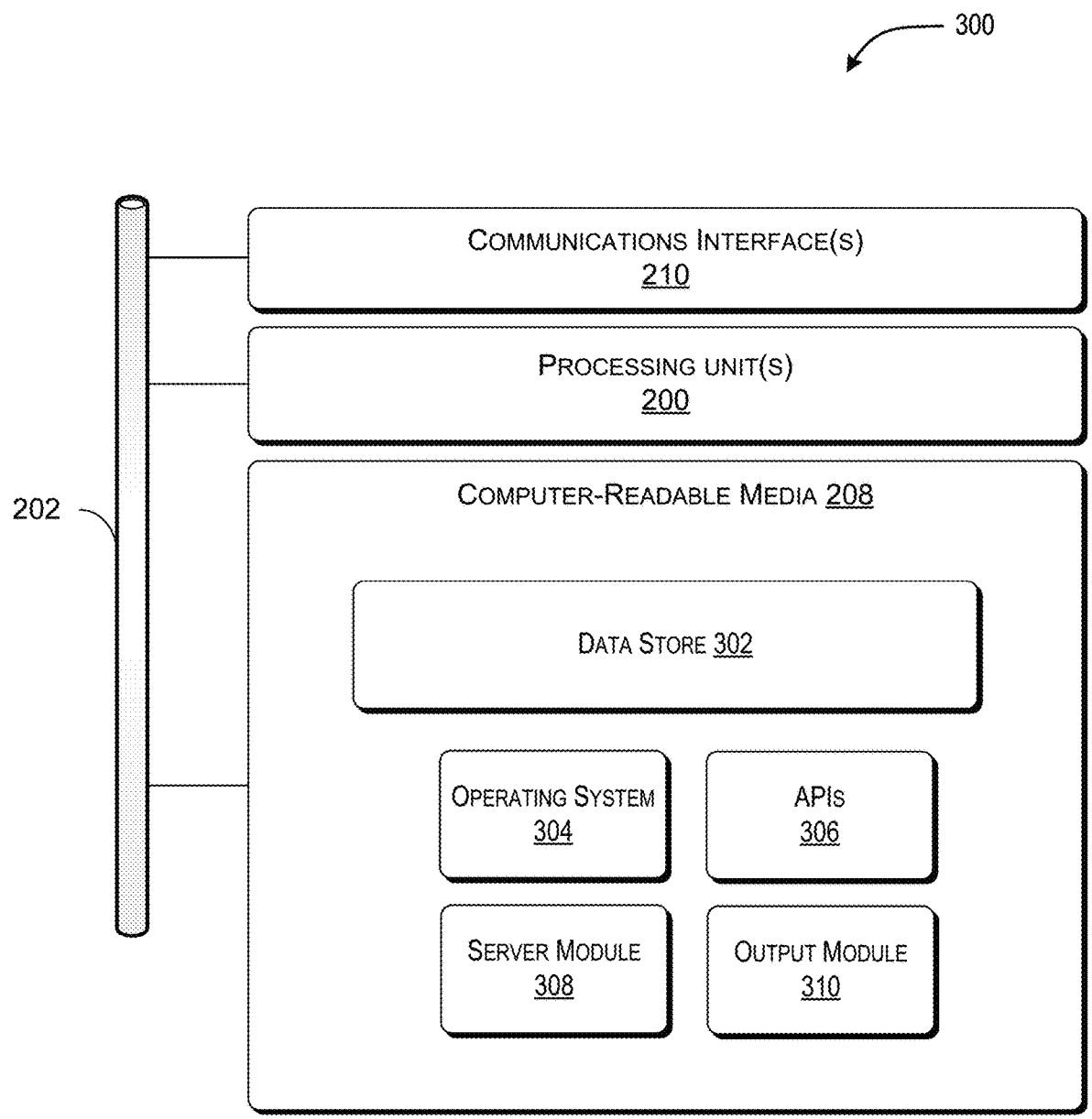
FIG. 3 is a system block diagram of an example of an implementation of components of the SBC system, shown in FIGS. 1 and 2, in accordance with the present disclosure.

Turn to FIG. 3, a system block diagram of an example of an implementation of components 300 of the SBC system 100 is shown in accordance with the present disclosure. The components 300 are configured to enable the SBC system 100 to securely collect and record data from the user 112 associated with a secure transaction. The components 300 may represent one or more of the devices shown in FIG. 2 that include, for example, the one or more processing units 200, system bus 202, memory 206, computer-readable media 208, one or more communication interfaces 210, camera encoder 216, fingerprint template encoder 224, device key 228, and privacy encoder 230. The components 300 are in signal communication and operatively connected, for example, via the system bus 202, which may include one or more of a system bus, a data bus, an address bus, a PCI bus, a Mini-PCI bus, and any variety of local, peripheral, and/or independent buses.

As utilized herein, processing unit(s), such as the processing unit(s) 200 may represent, for example, a CPU-type processing unit, a GPU-type processing unit, a field-programmable gate array ("FPGA"), another class of digital signal processor ("DSP"), or other hardware logic components that may, in some instances, be driven by a CPU. For example, and without limitation, illustrative types of hardware logic components that may be utilized include Application-Specific Integrated Circuits ("ASICs"), Application-Specific Standard Products ("ASSPs"), System-on-a-Chip Systems ("SOCs"), Complex Programmable Logic Devices ("CPLDs"), etc.

As utilized herein, computer-readable media, such as computer-readable media 208, may store instructions executable by the processing unit(s) 200. The computer-readable media may also store instructions executable by external processing units such as by an external CPU, an external GPU, and/or executable by an external accelerator, such as an FPGA type accelerator, a DSP type accelerator, or any other internal or external accelerator. In various examples, at least one CPU, GPU, and/or accelerator is incorporated in a computing device, while in some examples one or more of a CPU, GPU, and/or accelerator is external to a computing device.

Computer-readable media may include computer storage media and/or communication media. Computer storage media may include one or more of volatile memory, non-volatile memory, and/or other persistent and/or auxiliary computer storage media, removable and non-removable computer storage media implemented in any method or technology for storage of information such as computer-readable instructions, data structures, program modules, or other data. Thus, computer storage media includes tangible and/or physical forms of media included in a device and/or hardware component that is part of a device or external to a device, including but not limited to random-access memory ("RAM"), static random-access memory ("SRAM"), dynamic random-access memory ("DRAM"), phase change memory ("PCM"), read-only memory ("ROM"), erasable programmable read-only memory ("EPROM"), electrically erasable programmable read-only memory ("EEPROM"), flash memory, compact disc read-only memory ("CD-ROM"), digital versatile disks ("DVDs"), optical cards or other optical storage media, magnetic cassettes, magnetic tape, magnetic disk storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

The one or more communication interfaces 210 may represent, for example, network interface controllers ("NICs") or other types of transceiver devices to send and receive communications over a network.

In the illustrated example, computer-readable media 208 includes the data store 302. In some examples, the data store 302 includes data storage such as a database (including a blockchain structure), data warehouse, or other type of structured or unstructured data storage. In some examples, the data store 302 includes a corpus and/or a relational database with one or more tables, indices, stored procedures, and so forth to enable data access including one or more of hypertext markup language ("HTML") tables, resource description framework ("RDF") tables, web ontology language ("OWL") tables, and/or extensible markup language ("XML") tables, for example.

The data store 302 may store data for the operations of processes, applications, components, and/or modules stored in computer-readable media 208 and/or executed by one or more processing units 200 and/or accelerator(s).

In this example, the computer-readable media 208 also includes operating system 304 and application programming interface(s) (APIs) 306 configured to expose the functionality and the data of the components 300 to external devices associated with the SBC System 100. Additionally, the computer-readable media 204 includes one or more modules such as the server module 308 and an output module 310, although the number of illustrated modules is just an example, and the number may vary higher or lower. That is, functionality described herein in association with the illustrated modules may be performed by a fewer number of modules or a larger number of modules on one device or spread across multiple devices.

Figure 4:
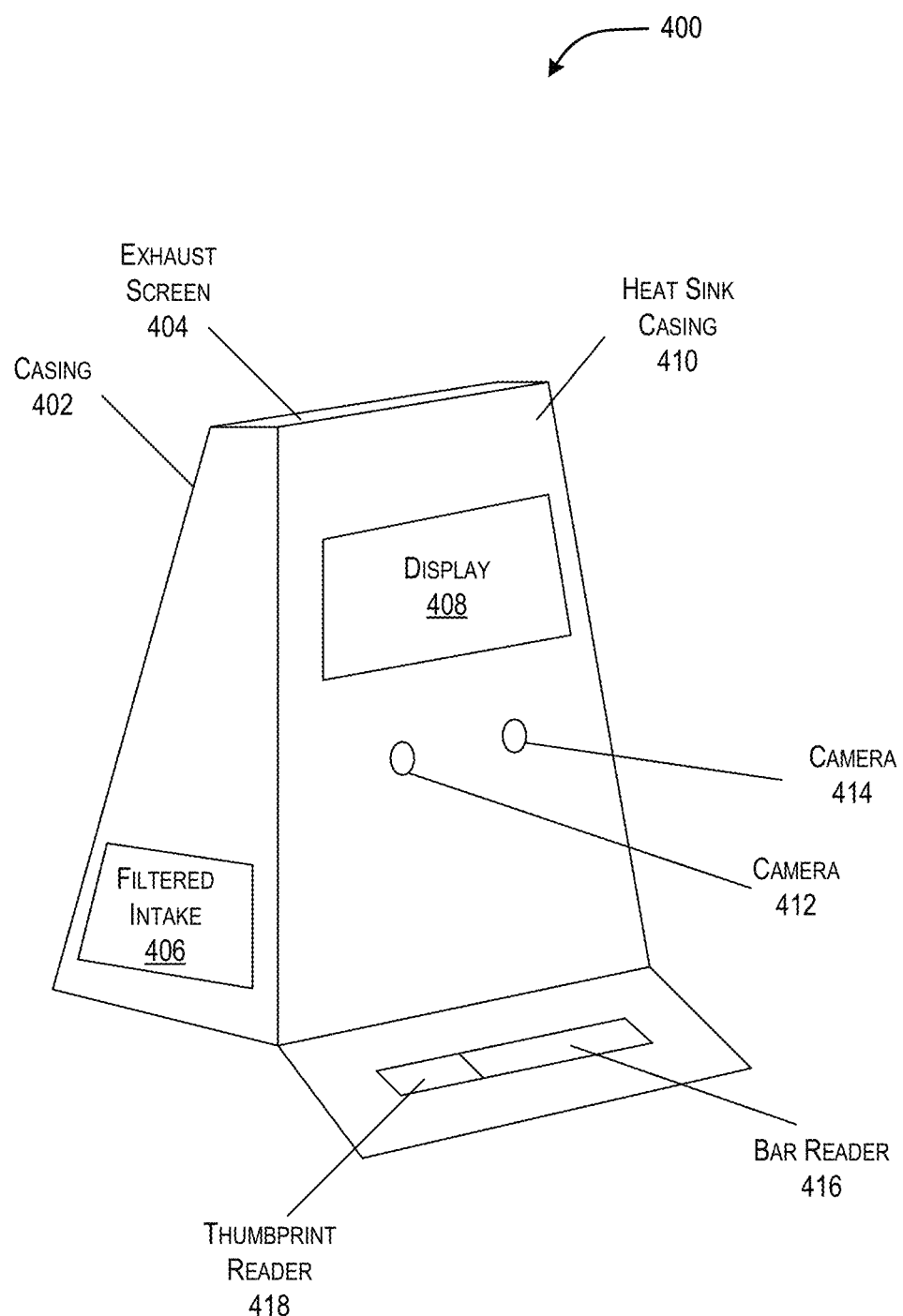
FIG. 4 is a perspective front view of an example of an implementation of the SBC system, shown in FIGS. 1 and 2, in accordance with the present disclosure.

FIG. 4, a perspective front view of an example of an implementation of the SBC system 400 is shown in accordance with the present disclosure. In this example, the SBC system 400 includes a casing 402 (i.e., a housing), an exhaust screen or vents 404, a filtered intake 406 to remove particulate matter and improve reliability of the device in hot and/or dusty field conditions, a display 408 to display instructions for a user 112, a heat-sink casing 410 (which, for example, may be constructed of metal) to dissipate camera heat or the like, a first camera 412 and an optional second camera 414, where the first camera 412 may be configured to sense normal visible spectrum light and the optional second camera 414 may be configured to sense thermal, infrared or non-visible spectrum light, for example.

The SBC system 400 further includes a fingerprinting portion including, for example, a bar reader 416 configured for multiple-finger scanning and a thumbprint reader 418 configured for thumb or single-finger scanning. The SBC system 400 alternatively include a first fingerprint scanner (not shown but described in FIG. 2) and an optional second fingerprint scanner (not shown but described in FIG. 2).

In this example, casing module 402 of the SBC system 400 may have generally trapezoidal shape in its side view and substantially rectangular shape in its front view. It is appreciated to those of ordinary skill in the art that these shapes are for example purpose only and the casing module 402 may vary significantly based on its design and intended use. The exhaust screen or vents 404 may be formed towards the top and/or side parts of the SBC system 400, through which heated or exhaust air flows outwards. The intake vent filter 406 may be formed towards the bottom part of the casing module 402, through which ambient air flows inwards.

The display screen 408 may be positioned and located on the front face of the SBC system 400 with a generally rectangular shape. The first camera 412 and optional second camera 414 may be position below the display screen 408 where the two cameras 412 and 414 are aligned in the horizontal direction. In this example, the first camera 412 is for visible light and the second camera 414 is for non-visible light, such as infrared or ultraviolet light, but not limited thereto.

The heat-sink casing 410 may be constructed of high thermal conductivity material to dissipate the heat generated by the cameras 412 and 414 and other components of the SBC system 400. In this example, the heat-sink casing 410 may be constructed of metal. The fingerprint collecting module may be positioned at the bottom part of the SBC system 400. The fingerprint collecting module may include at least two fingerprint readers, a first fingerprint reader 416 and a second fingerprint reader 418 that are located adjacent to each other. Among the two fingerprint readers, one fingerprint reader may have an elongated shape that is configured for multiple-finger scanning, while the other fingerprint reader may be configured for single-finger scanning, such as, for example, thumb scanning.

Figure 5:
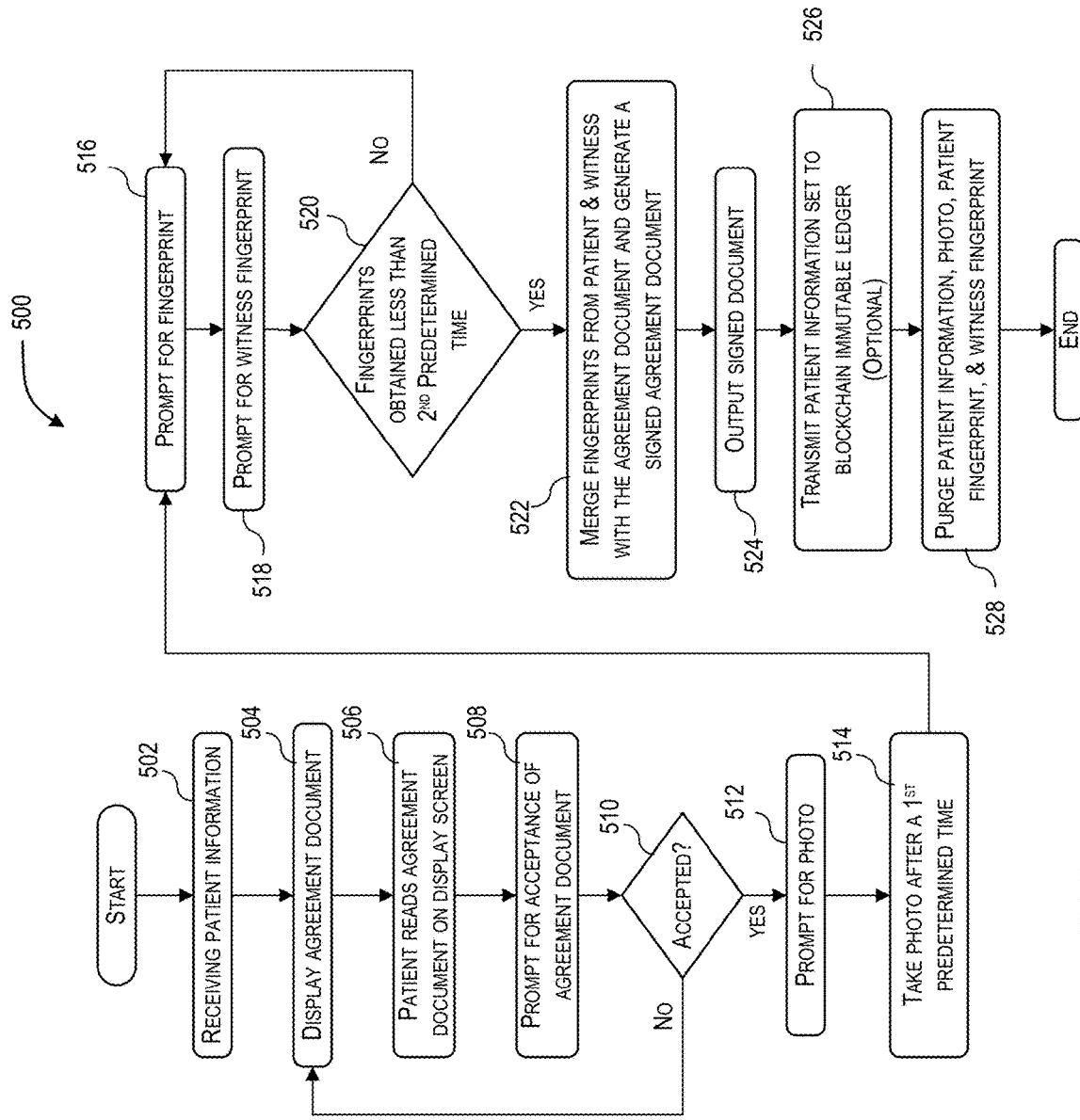
FIG. 5 is a flowchart diagram for an example of an implementation of a collecting method performed by the SBC system, shown in FIGS. 1 and 2, in accordance with the present disclosure.

As an example of operation, FIG. 5 is a flowchart diagram for an example of an implementation of a collecting method 500 performed by the SBC system 100 in accordance with the present disclosure. The method 500 begins 502 by the SBC system 100 receiving a user's 112 personal information. In this example, the method 500 is related to a medical provider and the user 112 is a patient that is attempting to receive medical services from the medical provider. The SBC system 100 then produces and displays 504 an agreement document on the display 238 for the user 112 to accept and digitally sign via biometric inputs. The user 112 then reads the agreement document that is displayed on the display 238. The SBC system 100 then prompts 508 the user 112 for acceptance of the terms of the agreement document. In decision step 510, if the user 112 does not accept the agreement document, the method returns to step 504 and the agreement document is again displayed on the display 238.

If, instead, the user 112 does accept the agreement document, the SBC system 100 prompts 512 the user 112 for a photograph and/or video recording. The user 112 may be informed to not move for a first predetermined time and at the expiration of the first predetermined time, the SBC system 100 takes 514 a photograph and/or records video of the user 112 with at least the first camera 212. In this example, the first predetermined time may be, for example, between approximately three to five seconds. The SBC system 100 then prompts 516 the user 112 for a fingerprint and after the user 112 provides a fingerprint scan with the fingerprint scanner 220 the SBC system 100 prompts the witness 114 or service representative 110 for a fingerprint within a second predetermined time. The witness 114 or service representative 110 then provide a fingerprint scan with either the fingerprint scanner 220 or optional second fingerprint scanner 222. In this example, the SBC system 100 may first timestamp the time when the fingerprint scan of the user 112 is received and again second timestamp the time when the fingerprint scan of the second person is received. Moreover, in this example, the second predetermined time may be, for example, approximately 1000 milliseconds. The SBC system 100 then determines if the second fingerprint scan provided by either the witness 114 or service representative 110 was obtained within the second predetermined time by comparing the first and second timestamps. In decision step 520, if the SBC system 100 determines that the second fingerprint scan was obtained after the second predetermined time, the method then returns to step 516 and the SBC system 100 again prompts 516 the user 112 and prompts 518 the second person for their fingerprints. The SBC system 100 again determines if the second fingerprint scan was obtained after the second predetermined time. If yes, the sub portion of the method between steps 515 to 520 repeats.

If, instead, the SBC system 100 determines that the second fingerprint scan was obtained within the second predetermined time after the fingerprint scan of the user 112 was obtained, the method continues to step 522. In step 522, the SBC system 100 merges the fingerprint scans from both the user 112 and the second person (i.e., either the witness 114 or service representative 110) with the agreement document and generates a signed agreement document. The SBC system 100 then outputs a copy of the biometrically "signed" agreement document with the display 238 and/or printer 240. Upon user's 112 instruction, the SBC system 100 can optionally transmit 526 the user's 112 information, photograph/video, scanned fingerprint, and the scanned fingerprint of the second person to a secured blockchain or immutable ledger or alternatively purges 528 these data without transmitting them to a secured blockchain or immutable ledger. The method 500 then ends.

In an example of operation, the SBC system 100 may record transactions in real-time such as may be required for auditing purposes. In general, the present disclosure relates to a collecting apparatus, such as segregated custom-purpose hardware but not limited thereto, that reads, encodes and records a user's 112 biometric data, and purges all raw and intermediate biometric data once finalized or encrypted data has been provided for secure storage or an immutable ledger like a blockchain. The SBC system 100 may delete the original biometric data upon delivery of "signed" agreement document to the storage device 204. The "signed" agreement document and the resulting biometric data in an encoded and encrypted data set may be transmitted to remote secure storage or an immutable ledger at the secure server 104 for permanent storage. In this example, the SBC system 100 may encrypt (i.e., scramble and encode) the private information in a manner that cannot be reasonably deciphered outside of the SBC system 100. This may allow for permanent storage at the secure server of such biometric information, such as scrambled without external cipher keys but not limited thereto, with reduced risk of compromise by, for example, code viruses, theft and/or loss of system data from cloud, private network, or insurance industry data warehouse systems.

While various embodiments have been shown for descriptive purposes, it shall be understood by those of ordinary skill in the art that such and like embodiments may be adapted to complex systematic and biometric workflow systems, for example. Moreover, there are numerous possibilities and variations in the medical, finance and other marketplaces to which embodiments of the present disclosure may be directly applied or reasonably adapted.

For example, the SBC system 100 may include the first camera 212 and the optional second camera 214. In this example, one of the two cameras 212 or 214 may be for visible light and the other for non-visible light, and the two cameras 212 and 214 may be aligned to take a photograph and/or record video in the same direction. Furthermore, the fingerprint scanner 220 may include two fingerprint readers, where one of the two fingerprint readers is for one finger, such as a thumbprint reader, and the other fingerprint reader is for multiple fingers such as a fingerprint bar reader. Moreover, the two fingerprint readers may be located proximate to each other so that two or more immediate or substantially simultaneous fingerprints can to be generated from the plurality of fingerprint readers.

In this disclosure, the collecting methods described may be applied to private information including, for example in a medical provider example, the name of patient/user 112, identifying number of patient, and/or date of birth of patient, where the response includes an affirmative response or a negative response. The collecting method may be applied where the certain time period is, for example, 10 seconds. The collecting method may be applied where the two persons include, for example, the patient/user 112 and a witness 114 or service representative 110.

Using the SBC system 100 and example method together as described herein, patient privacy may be protected while recording highly private personal data about each individual. This is a challenging application, particularly considering that high-level government and insurance industry regulations already require, in a systematic way, collection of biometric information such as fingerprints, photographic images, and other data based upon personal characteristics of individuals.

In this disclosure, the SBC system 100, or parts thereof, may be implemented in dedicated hardware and/or software without limitation. For example, while a highly-specific, specialized apparatus is provided to protect patient privacy while recording private and personal data about an individual, at least some of the functionality may optionally be embodied in software. Such solutions are adaptable based on specific requirements, such as, for example, government and/or industry regulations or goals, where collecting biometric information is either an end-goal or but a small step in a larger process. For example, positive identification readers may improve safety and facilitate audits of potential financial fraud abuses in complex high-value industries. Along with the adoption of blockchain structure, any new data or fraud abuses may be identified instantaneously by the user or the custodian of the data located on the distributed blockchain network.

It is appreciated by those of ordinary skill in the art that embodiments of the present disclosure may incorporate existing fingerprint reader devices, biometric lock devices, access-authorization-auditing electronic system access controls, and healthcare data processing systems and databases. For example, embodiments may be adapted for computing devices with integrated fingerprint readers, fingerprint reader hardware in law enforcement and customs identification applications, biometric door locks, systematic face scanning and/or facial recognition, financial industry transaction systems, security agency hardware encryption, or the like.

As an example, turning back to FIG. 4, the SBC system 400 may be disposed in a sealed enclosure, such as for intermittent use and/or with an external heat-sink. As described earlier, the SBC system 100 may include a casing module, a display screen 408 which displays written instructions provided to the patient, a metal heat-sink casing for dissipating camera heat, one or two cameras 412 or 414 for acquiring images based on normal visible light as well as thermal, infrared or non-visible-light, a fingerprint bar reader 416 for multiple-finger scanning; and a thumbprint reader 418 for thumb or single-finger scanning.

The SBC system 400 may have a trapezoidal shape in its side view and a substantially rectangular shape in its front view, or may be shaped differently to increase surface area for heat dissipation. The display screen 408 is preferably provided in the front face of the SBC system 400 and may have a rectangular shape. The camera 412 is provided below the display screen 408, including in the two different cameras 412 and 2414 aligned in the height or vertical direction, where one of the two cameras 412 or 414 is for visible light and the other is for non-visible light. The casing 402 is made of material that readily dissipates heat generated by the camera 412 and 414, and is preferably made of metal.

In this example, fingerprint scanner is located at a bottom part of the SBC system 400, including at least one of the two fingerprint readers 416 and 418, which are located adjacent to each other. Among the two fingerprint readers 416 and 418, one fingerprint reader (i.e., bar reader 416) which may have a more elongated shape may be used for multiple-finger scanning, while the other fingerprint reader (i.e., thumbprint reader 418) may be used for single-finger scanning, such as, for example, thumb scanning. A sensor data purging module is provided inside the casing 402, and configured to purge all temporary data acquired by the photo collecting module and the fingerprint collecting module.

In general, the SBC system 400 includes acquisition hardware and other hardware mechanisms such as at least one encoding and/or recoding device, which operate in unison where raw biometric data is input. This unprotected data is encoded by hardware and/or software before delivery to temporary storage (i.e., storage device 204) based on an encryption chip mechanism. The SBC system 400 utilizes the private encryption key 228 which is known only to the SBC system 400. The hardware encryption apparatus, and the hardware encryption mechanism, may comprise a uniquely coded privacy encoder chip.

In this example, the method performed by the SBC system 400 demonstrates how a private biometric signature may be used to confirm a real-time medical transaction. For the prevention of medical fraud, the method steps demonstrate how a patient/user 112 may review a document and then certify with a witness 114, using a dedicated real-time apparatus with hardware encryption in this example. Further, the biometric information of both the patient/user and the witness may be recorded on the immutable ledger such as a blockchain. In the event of a fraud occurs, the fraudulent transaction can be immediately pin-pointed by locating the new block of data that contains fraudulent actor's information.

Similar to the previous discussion, the SBC system 400 performs a method that includes receiving patient information, generating an agreement document that is displayed on the display 408 for the patient to read. Then, the SBC system 400 reads, records and encodes, prompts for acceptance or non-acceptance. If the patient matching the biometric data acknowledges and accepts the document, a corresponding medical identification number is generated or input, and each of the patient's surname, given name, and date of birth are input or confirmed. Next, the SBC system 400 displays a countdown timer with optional instructions for a photograph, and at least one visible-light camera acquires a photographic image, which it saves to temporary storage (i.e., the storage device 204). Similarly, the non-visible-light camera acquires an image and saves that in temporary storage as well. The photographic encoder chip combines and/or hashes the two photographic images into a combined data set, and forwards the combined data set, including the encoded private photographic images, to a privacy encoder temporary storage area on the storage device 204.

The SBC system 400 also displays instructions for fingerprint capture, and actuates at least one fingerprint scan. It processes the fingerprint scan into a fingerprint template data set; and a fingerprint encoder chip forwards a combined data set including unencrypted fingerprint template data to the privacy encoder temporary storage. The privacy encoder communicates with a device key chip delivering an encryption key unique to session recording, and then combines and independently encrypts all data acquired including agreement, patient name, date of birth, patient responses, encoded photographic image data, and encoded fingerprint template data into an encrypted data set. The SBC system 400 purges all temporary data including unencrypted photographic images, fingerprint scans, and fingerprint templates such that the combined mechanisms delete original biometric data within the SBC system 400 upon delivery to the secure server 104 that could be embedded with a blockchain structure and/or software. Thus, the SBC system 400 delivers the resulting biometric data in an encoded and/or encrypted data set to the secure server 104 for permanent storage.

In general, the SBC system 400 is a hardware encryption device that is preferably embodied in a compact, durable form including a camera module having a first camera for acquiring visible-light images and a second camera for acquiring non-visible-light images, such as infrared and/or ultraviolet, where the two cameras align to acquire images from substantially the same direction. The device includes a fingerprint module including a first fingerprint reader preferably for one finger, and a second fingerprint reader preferably for multiple fingers, where the second fingerprint reader is preferably located proximate to the first fingerprint reader. A privacy module includes a first chip that converts acquired photographic images into an encoded photo data set, and a second chip that converts acquired fingerprints into an encoded fingerprint data set template. A device key chip is connected to the privacy module for providing a unique encoded symmetric device key. A hardware encryption processor (which may be one of the one or more processing units 200 or a separate processor) is connected to the privacy module. All modules are physically separated with hardware connection boundaries that precludes malicious virus software, or the like, such that only the hardware encryption processor is connected to any computing main board.

In this example, the recording method is embodied within a compact device for completing a medical transaction declaration record, such that a real-time transaction encodes in a manner preventing forgery or tampering. The method includes activating at least two fingerprint readers that, when activated, requires two immediate and substantially simultaneous fingerprints. The device display prompts for camera photographic images, and then acquires photographic images with the cameras. The SBC system includes a hardware encryption module for encoding and encrypting of the recorded record data.

When the SBC system prompts for photographic images, the patient may wait a first predetermined time (such as, for example, 3-5 seconds) for the photographic images to be acquired; and, if the patient does not accept the document, the process returns back to the first step. After taking the photographic images successfully, the process goes on to the next step, where biometric fingerprints are required to confirm the identities of the patient and the witness. The fingerprints from these two persons are recorded on two physical reader devices. Next, the SBC system time-stamps each biometric fingerprint and electronically determines that the fingerprints were recorded within a certain time period defined by the second predetermined time that may be, for example, about one to 10 seconds.

The SBC system produces an "agreement document", such as using Portable Document Format (PDF), and stores it in device memory. It displays the "agreement document" on the device display 408. The SBC system then records an affirmative or negative response from the patient through the device display 408 and at least one user-selectable response. It prompts for biometric reader activation, and records biometric fingerprints from two persons, on, for example, two physical reader devices. The SBC system time-stamps each biometric fingerprint and electronically determines that that fingerprints were both recorded within the second predetermined time that may be, for example, between about 1 second to 10 seconds of each other.

The SBC system is configured to make an electronic decision about the physical proximity of the two people (i.e., how physically close are they to each other), such as one patient/user 112 and one witness 114, based upon the first fingerprint reader time-stamp and the second fingerprint reader time-stamp. If the SBC system determines that the fingerprints were recorded within a predetermined period, such as 10 seconds or less, the SBC system merges the biometric signatures from the two persons with the "agreement document," thereby generating the "signed agreement document." However, if SBC system determines that the fingerprints were not recorded within 10 seconds of each other, the process returns to the fingerprint scan step and the process repeats. When the SBC system has merged the biometric signature in the signed agreement document, the signed agreement document is output to the user 112 and sent to the secure server 104 and the process is complete.

Figure 6:
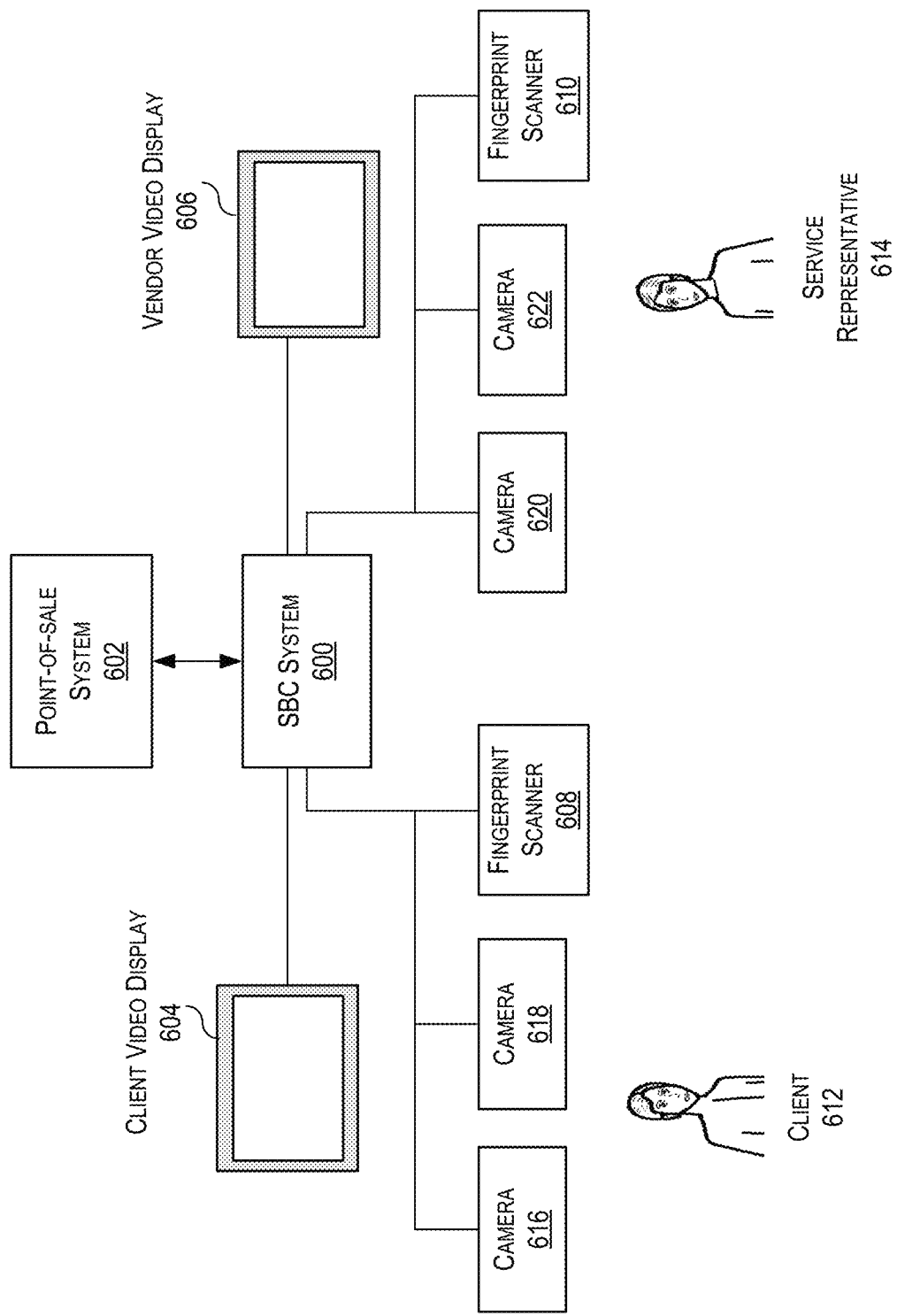
FIG. 6 is a system block diagram of an example of an implementation of SBC system, shown in FIGS. 1 and 2, for a point-of-sale application in accordance with the present disclosure.

FIG. 6 is a system block diagram of an example of an implementation of the SBC system 600 for a point-of-sale application on a point-of-sale system 602 for purchasing various materials or non-fungible transactions in accordance with the present disclosure. In this example, the SBC 600 is in signal communication with the point-of-sale system 602 and a client video display 604 and a vendor video display 606. The client video display 604 is a display monitor having a 180-degree viewing range and the vendor video display 606 is another display monitor also having a 180-degree viewing range. In this example, the client video monitor 604 and vendor video display 606 may be oriented such that both monitors are facing opposite to each other. In general, the client video display 604 and vendor video display 604 are configured to simultaneously display the same identical transactional data. This may be accomplished via specialized hardware circuitry, software, or both within the SBC system 600. In general, the SBC system 600 controls both the outputs to the client video display 604 and vendor video display such that both monitors display mirrored content from the SBC system 600 and point-of-sale system 602. In this example, the SBC system 600 may include biometric capture readers such as, for example, the first fingerprint scanner 608 and second fingerprint scanner 610. In this example, the first fingerprint scanner 608 may be utilized by a client 612 (i.e., a user) that desires to purchase the material or enter into various non-fungible transactions with a vendor. The second fingerprint scanner 610 may be utilized by a service representative 614 of the vendor. Similarly, the client video display 604 is configured to be utilized by the client 612 and the vendor video display 606 is configured to be utilized by the service representative 614. In addition to the fingerprint scanners 608 and 610, the SBC system 600 may be in signal communication with a first visual spectrum camera 616, a first non-visual spectrum camera 618, a second visual spectrum camera 620, and a first non-visual spectrum camera 622, respectively. In this example, the first visual spectrum camera 616 and the first non-visual spectrum camera 618 may be configured to record photographs and/or video of the client 612 and the second visual spectrum camera 620 and the second non-visual spectrum camera 622 may be configured to record photographs and/or video of the service representative 614. Moreover, while not shown, it is appreciated that the SBC system 600 may further include one or more microphones to record the voices of the client 612, service representative 614, or both.

Figure 7:
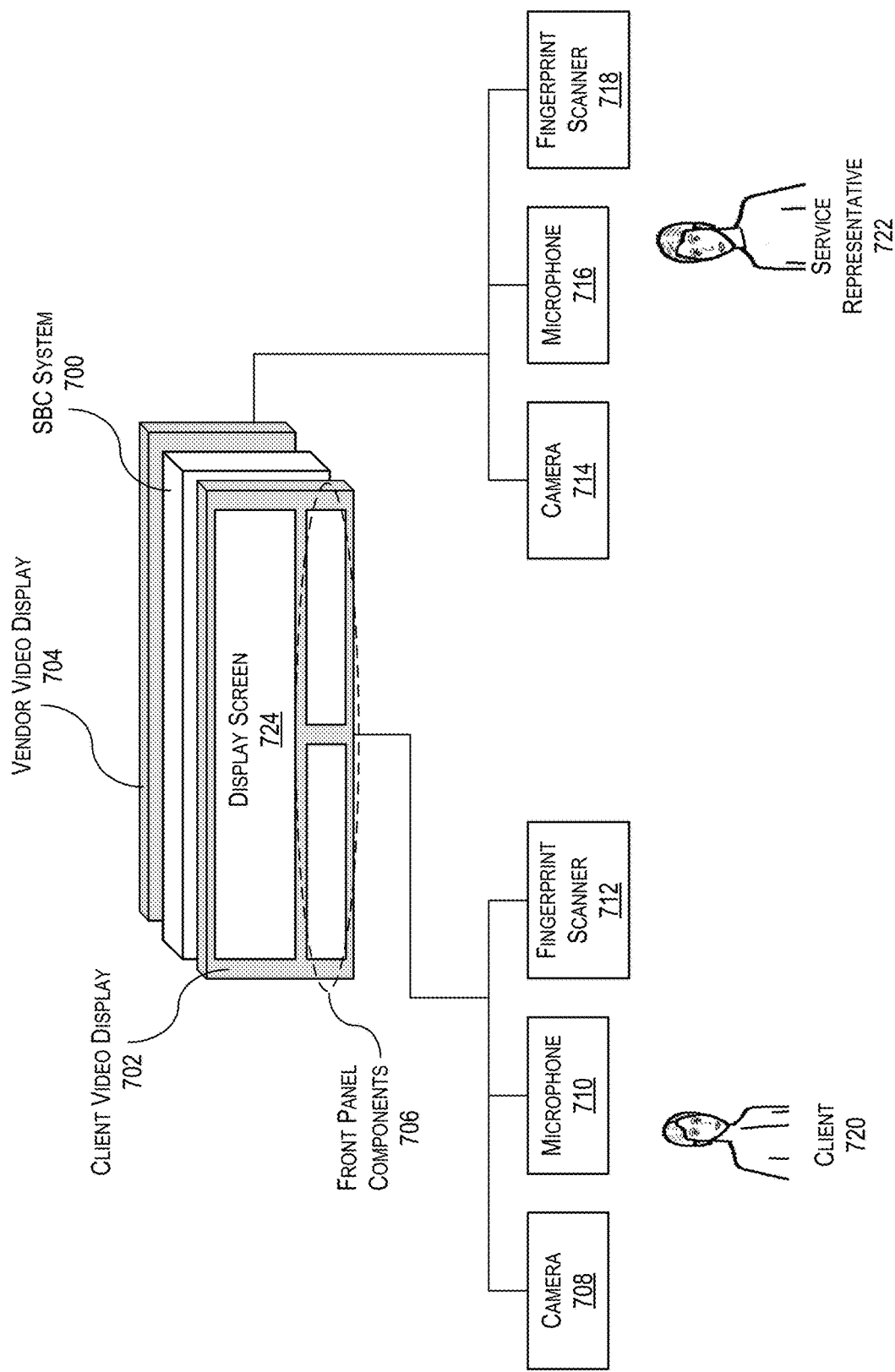
FIG. 7 is a system block diagram of an example of an implementation of the SBC system, shown in FIGS. 1 and 2, in a compact, audio-capture recorder form in accordance with the present disclosure.

FIG. 7 is a system block diagram of an example of an implementation of the SBC system 700 in a compact, audio-capture recorder form in accordance with the present disclosure. In this example, the SBC system 700 and may be in signal communication with or include a point-of-sale system. The SBC system 700 is in signal communication a client video display 702 and vendor video display 704. In this example, the client video display 702 includes front panel components 706 and the vendor video display 704 also includes back panel components (not shown). The front panel components 706 includes a camera 708, microphone 710, and fingerprint scanner 712. Similarly, the back panel components include a camera 714, microphone 716, and fingerprint scanner 718. The front panel components 706 are configured to be utilized by a client 720 and the back panel components are configured to be utilized by a service representative 722. In this example, the SBC system 700 may optionally not include the camera 708 and camera 714 and, instead, capture voice or audio recordings in addition to hand and fingerprints with the microphone 710 and 716 and fingerprint scanners 712 and 718. Such variation provides simplicity in design and function. In this example, the combination of SBC system 700 and client video display 702 includes a front panel including a display screen 724 and the front panel components 706 includes human interface readers, specifically at-least microphone 710 and biometric hardware reader device such as, for example, the camera 708 and the fingerprint scanner 712. In this example, the combination of SBC system 700 and vendor video display 704 includes a back panel including a display screen (not shown) and the back panel components includes human interface readers, specifically at-least microphone 714 and biometric hardware reader device such as, for example, the camera 716 and the fingerprint scanner 718. Similar to the last example, the client video display 702 and vendor video display 704 are oriented opposite each other. In this example, the SBC system 700, and client video display 702, and vendor video display 704 may include a waterproof sealant membrane designed for application of chlorides or alcohol based cleaner solutions without damaging internal electronics.

Figure 8:
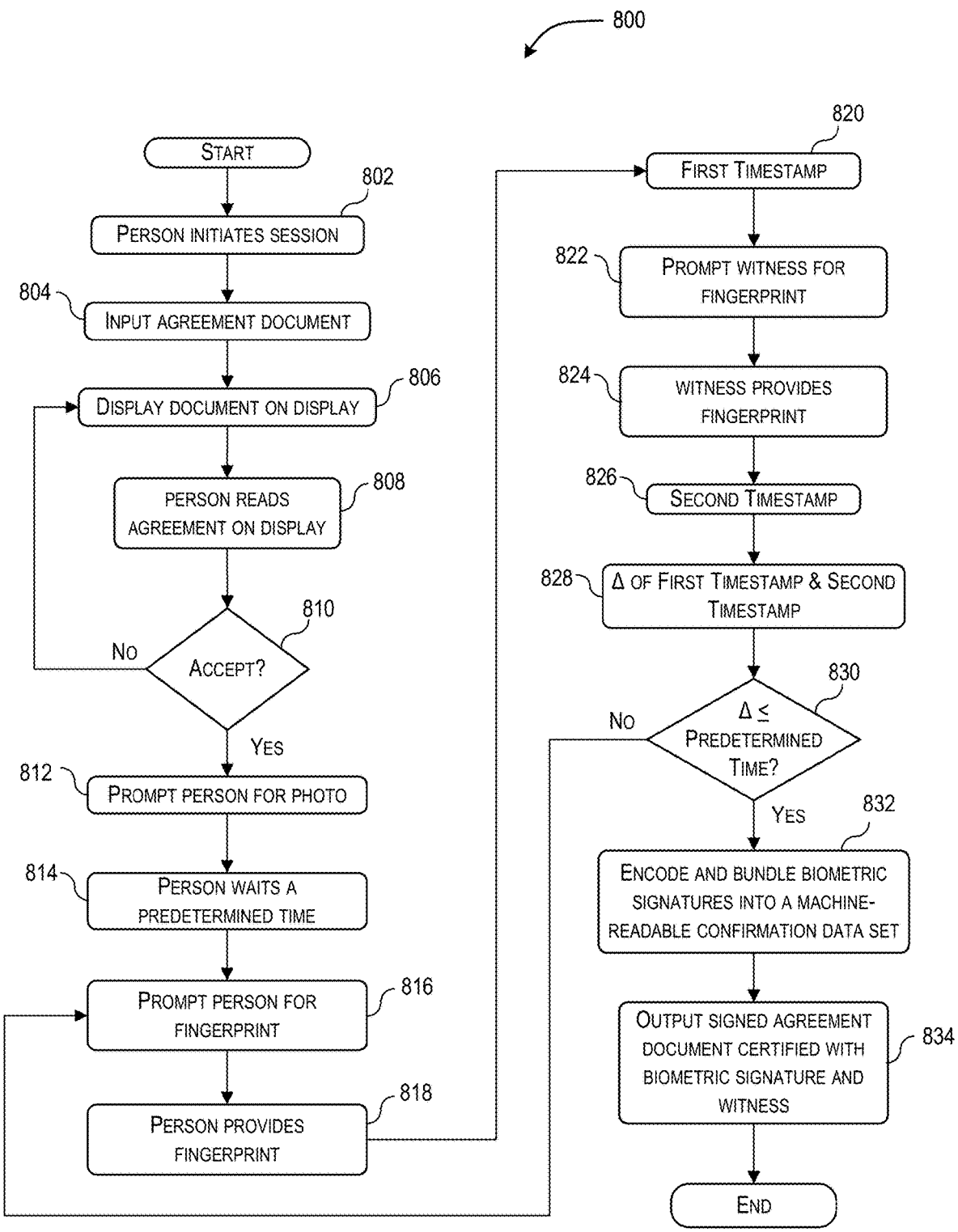
FIG. 8 is a flowchart diagram for an example of an implementation of a method for encoding private biometric data into an audit record in accordance with the present disclosure.

FIG. 8 is a flowchart diagram for an example of an implementation of a method 800 for encoding private biometric data into an audit record in accordance with the present disclosure. The method 800 starts by the user 112 initialing 802 a session on the SBC system. The SBC system queries the user 112 for their information in generating an agreement document and the user 112 inputs 804 the requested information. Once the information from the user 112 has been entered, the SBC system displays 806 (for example, and a screen of a display system of the SBC system) the completed agreement document for the user 112 to review. The user 112 then reads 808 the agreement document on the display and, in decision step 810, the SBC system queries the user 112 to accept the agreement document. If the user 112 does not accept the agreement document, the SBC system returns to step 806 and again displays the agreement document for the user to accept and then again queries the user 112 to accept the agreement document. If the user 112 continues to not accept the agreement document, the SBC system may optionally end the session.

If, instead, the user 112 accepts the agreement document, the SBC system then prompts 812 the user 112 that a photograph and/or video recording will be obtained with the camera after a predetermined time that may be, for example, 3-5 seconds and then then the user waits 814 the predetermined time and the SBC system takes a picture or video of the user 112. The SBC system then prompts 816 the user 112 for a fingerprint and the user 112 then provides a fingerprint with the fingerprint scanner. Once the SBC system receives the fingerprint from the user 112, the SBC system timestamps 820 the scanned fingerprint with a first timestamp. The SBC system then prompts 822 a second person for a fingerprint and the second person then provides 824 their scanned fingerprint. Once the SBC system receives the fingerprint from the second person, the SBC system timestamps 826 the scanned fingerprint with a second timestamp. The SBC system then calculates 828 the difference in time between the first timestamp and the second timestamp and then determines if the difference in time is less than or equal to a second predetermined time which may be, for example, about 1,000 milliseconds. If the difference in time is greater than the second predetermined time, the method 800 returns to step 816 and the SBC system again prompts the user 112 for a fingerprint and the method 800 repeats until decision step 830. If, instead, the difference is less than or equal to the second predetermined time, the SBC system encodes 832 and bundles the biometric signatures into a machine-readable confirmation data set that may be stored in storage device 204 or transmitted to a blockchain type immutable ledger. The signed agreement that is certified with biometric signatures of the user 112 and the second person is output 834 for the user 112 to review. The SBC system may then purge all of the biometric data and the method 800 ends. In this example, as described earlier, the second person may be a witness 114 or customer service representative 110.

Figure 9:
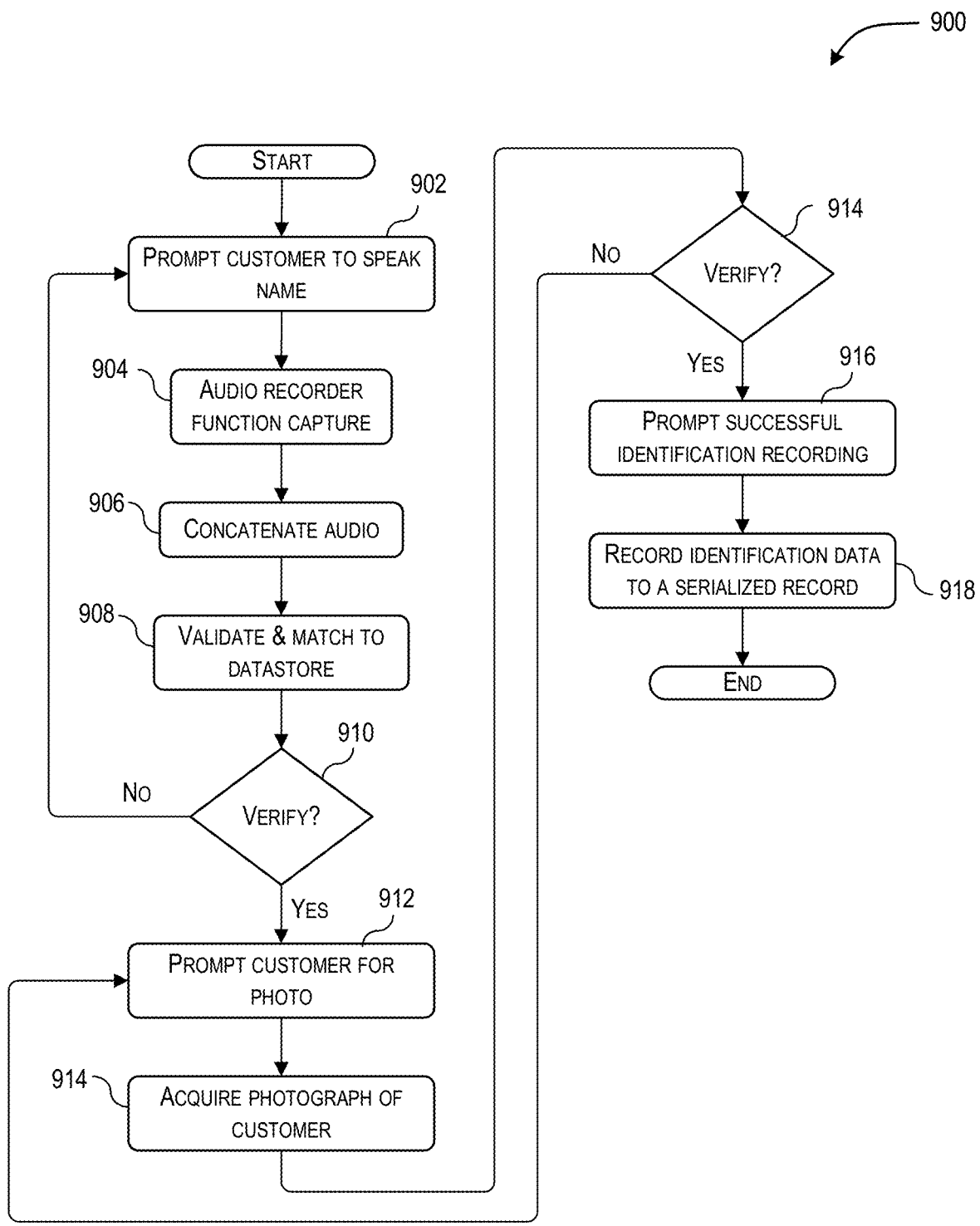
FIG. 9 is a flowchart diagram of an example of an implementation of a method for audio-capture recorder logic applied in compact the SBC system, shown in FIG. 7, in accordance with the present disclosure.

FIG. 9 is a flowchart diagram of an example of an implementation of a method 900 for audio-capture recorder logic applied in compact the SBC system 700 in accordance with the present disclosure. The method 900 starts by prompting 902 the customer (i.e., user 112/client 720) to speak their name with either video or audio instructions on the display screen 724 or over a speaker. The SBC system 700 then records 904 the customers voice with an audio recorder function capture and then performs 906 a quality, compaction, and noise removal via an electronic process generally referred to a concatenation. The SBC system 700 then validates 908 and matches the recorded audio to data in a database or private store and, in decision step 910, if the recorded audio is not validated, the method 900 returns to step 902 and the process repeats to decision step 910 because the SBC system 700 will either cancel the transaction or re-attempt to process the current transaction recording process.

If instead, the recorded audio is validated, the method 900 prompts 912 the customer for a photo and then acquires 914 a photograph of the customer utilizing a timer mechanism. In decision step 914, the SBC system 700 compares the acquired photograph to a private image database resulting in continuation, cancellation, or re-attempt of the existing transaction. If the verification fails, the process returns to step 912 and the SBC system 700 again prompts 912 the customer for a photo. The process then repeats to decision step 914. Additionally, the SBC system 700 can optionally transmit the cancelled attempt information to an immutable ledger (e.g., a blockchain) thus alert all the users located on the blockchain that an attempted fraud may have occurred.

If, instead, the verification passes, the SBC system 700 produces a system prompt 916 that indicates success of the recording and capture process. The SBC system 700 then forwards 918 the captured data through system bus, volatile memory to Audit Controller for processing, encoding, and permanent recording process. The method 900 then ends.

Figure 10:
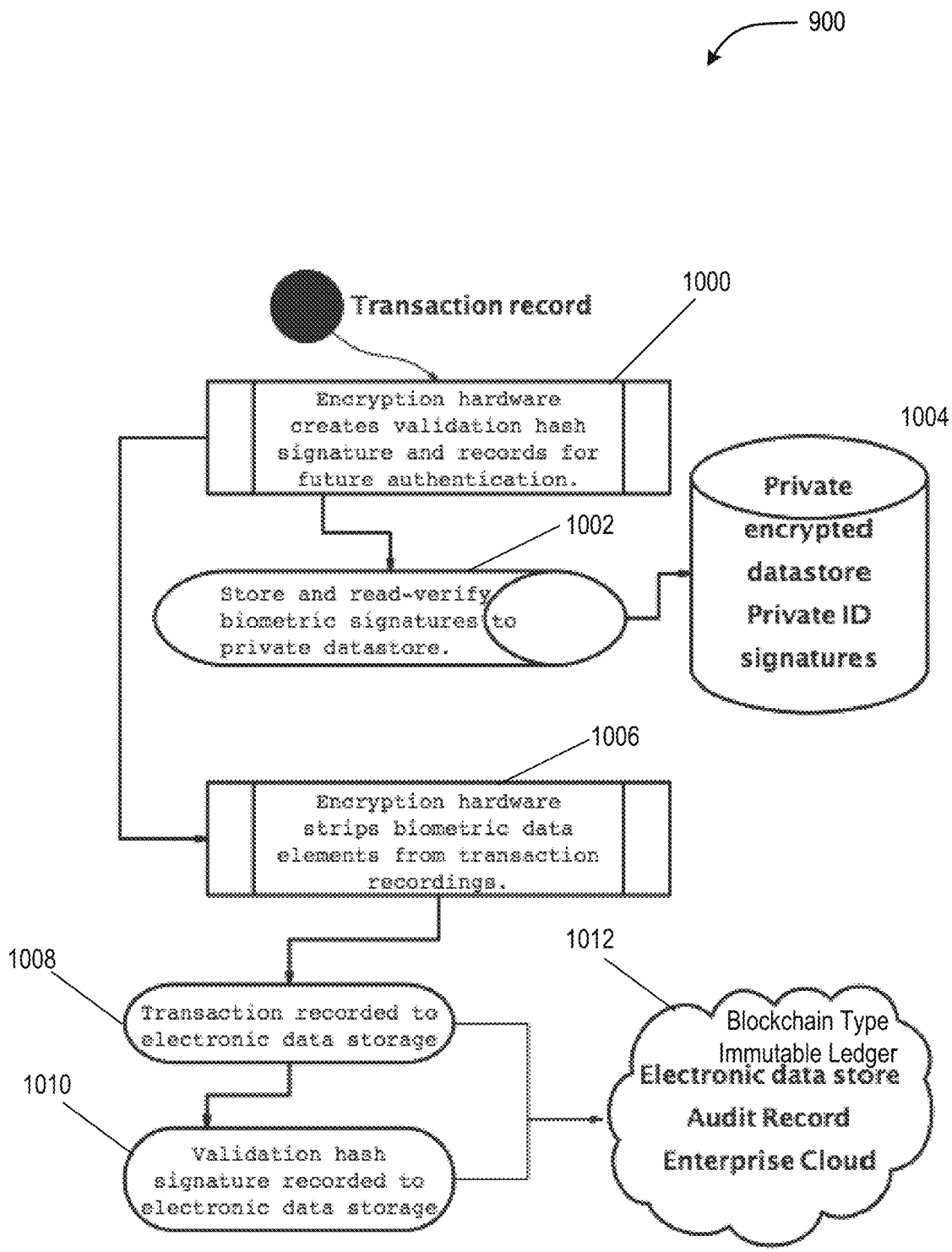
FIG. 10 is a system block diagram of an example of an implementation of a method for exporting audit record to a private encrypted electronic datastore in Cloud, an immutable ledger such as a blockchain and external applications that meet governmental privacy regulations for protection of biometric data in accordance with the present disclosure.

FIG. 10 is a system block diagram of an example of an implementation of a method for exporting audit record to electronic system data stores in Cloud and external applications that meet governmental privacy regulations for protection of biometric data in accordance with the present disclosure. In this example, the SBC system, block 1000 includes encryption hardware that creates a validation hash signature and records for further authentication. It utilizes a process that creates a validation hash which is uniquely serial to the captured biometric data recordings. The validation hash provides a permanent record audit trail for chain-of-custody (i.e., extended, and enhanced checksum mathematical function). Block 1002 includes a memory that stores and read-verifies biometric signatures to a private datastore. Block 1002 utilizes a process that outputs a recording to private data stores or database at datastore 1004, and additionally performs a Read-Verify function for a certification or the validation hash described earlier. The datastore 104 is a private encrypted datastore having private identification (ID) signature. This process ensures the integrity of, and private data store retained for future audit capability.

Block 1006 includes encryption hardware that strips the biometric data elements from the transaction recordings. In general, block 1006 provides an encoding and standardization of non-biometric data recordings for delivery to external or Cloud data stores and reporting systems. The data is exported and recorded in block 1008, where the transaction is recorded to an electronic data storage. The data is then passed to block 1010. In block 1010, the validation hash signature is recorded to an electronic data storage. As such, the exported data set include the certified validation hash appended and encoded with the data set. This process excludes any private biometric data from the validation hash and the data set that is not reversible to re-create private biometric data. In block 1012, the SBC system exports data set to cloud or external immutable ledger or data stores and reporting applications.

Figure 11:
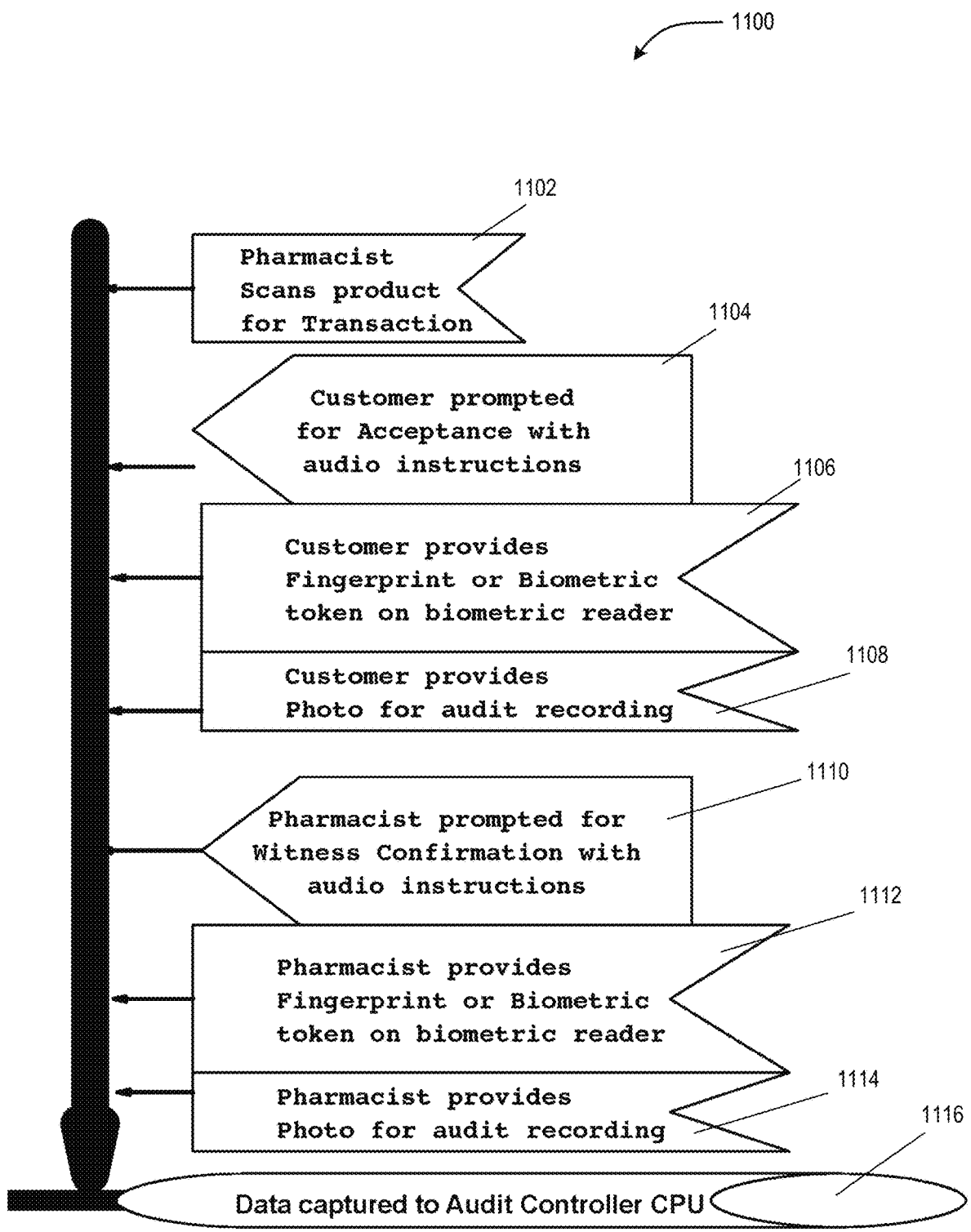
FIG. 11 is a flowchart of an example of an implementation of a method for data capture in accordance with the present disclosure.

FIG. 11 is a flowchart of an example of an implementation of a method 1100 for data capture in accordance with the present disclosure. In this example, the service representative 110 is a pharmacist and the user 112 is a customer at a pharmacy. The method 1100 begins by the pharmacist scanning 1102 a product for a transaction with the customer. The SBC system then prompts 1104 the customer for acceptance of the transaction with audio instructions. The customer then provides 1106 biometric data to the SBC system. The biometric data may be biometric recording from the customer indicating an affirmative response, a fingerprint, or biometric token on a biometric reader. The SBC system then prompts the customer for a photograph and the customer provides 1108 a photograph to accompany the audit recording. The SBC system then prompts 1110 the pharmacist for a witness confirmation with audio instructions. The pharmacist then provides 1112 a biometric capture that indicates acceptance as a witness of a face-to-face transaction with the customer. The biometric capture may be scanned fingerprint of the pharmacists, or biometric token on a biometric reader. The SBC system then may prompt the pharmacist for photograph and the pharmacist provides 1114 a photograph as an audio record for audit purposes. In step 1116, the SBC system aggravates the data and routes it to an audio controller for processing and encoding.

Figure 12:
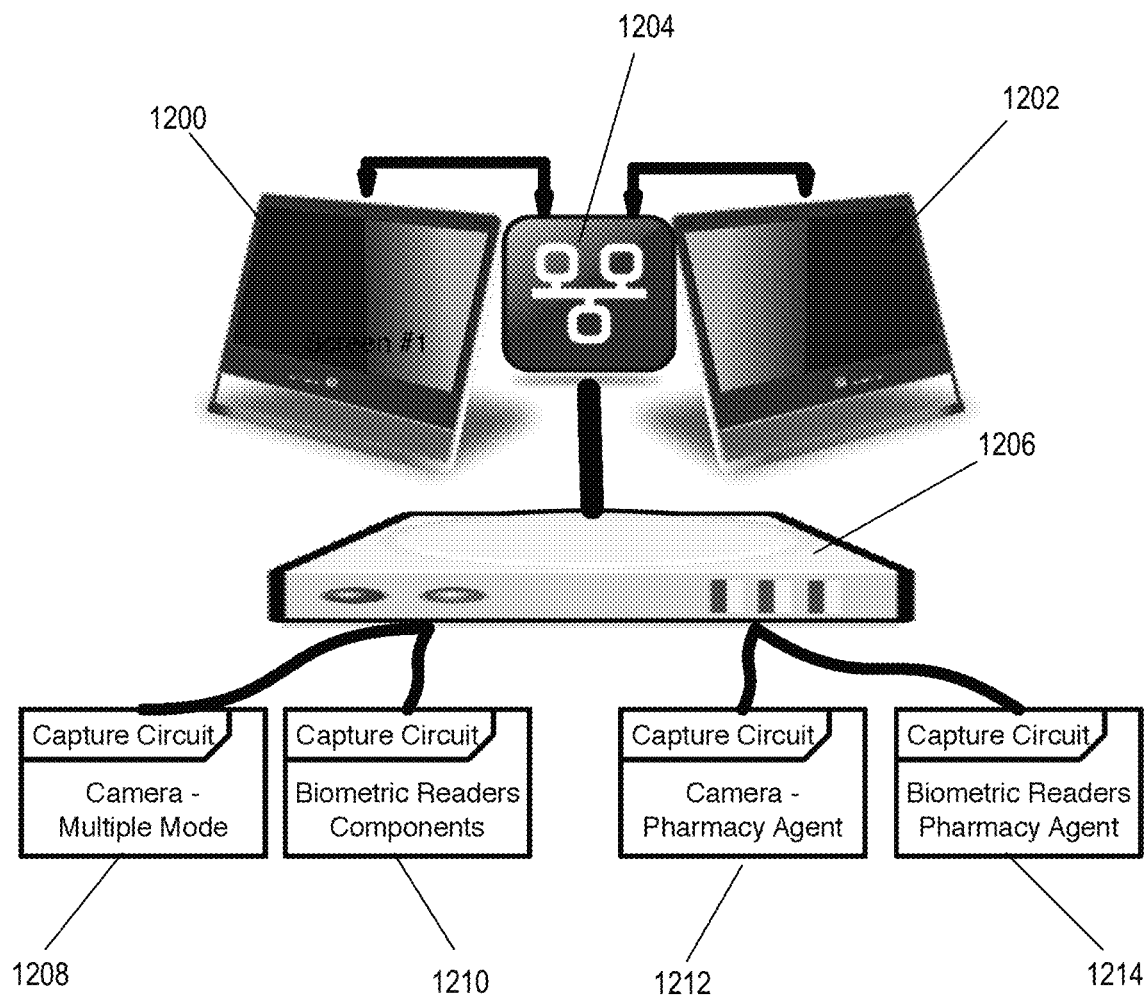
FIG. 12 is a system block diagram of an example of an implementation of hardware logic that delivers a guaranteed, tamper proof solid-state mirrored visual display with identical data content in accordance with the present disclosure.

FIG. 12 is a system block diagram of an example of an implementation of hardware logic that may deliver a guaranteed, tamper proof solid-state mirrored visual display with identical data content in accordance with the present disclosure. In this example, the SBC system includes a client video display 1200, vendor video display 1202, control circuit 1204, and second controller 1206. In this example, the control circuit 1204 may be a proprietary circuit, component, or device configured to control and recording and verification of the video displays 1200 and 1202. The controller 1206 may be an electronic controller that includes most of the components of the SBC system that have been discussed earlier. In this example, the controller 1206 may be in signal communication with cameras 1208 (for the customer) and 1210 (for the service representative) and biometric readers 1212 (for the customer) and 1214 (for the service representative).

Figure 13:
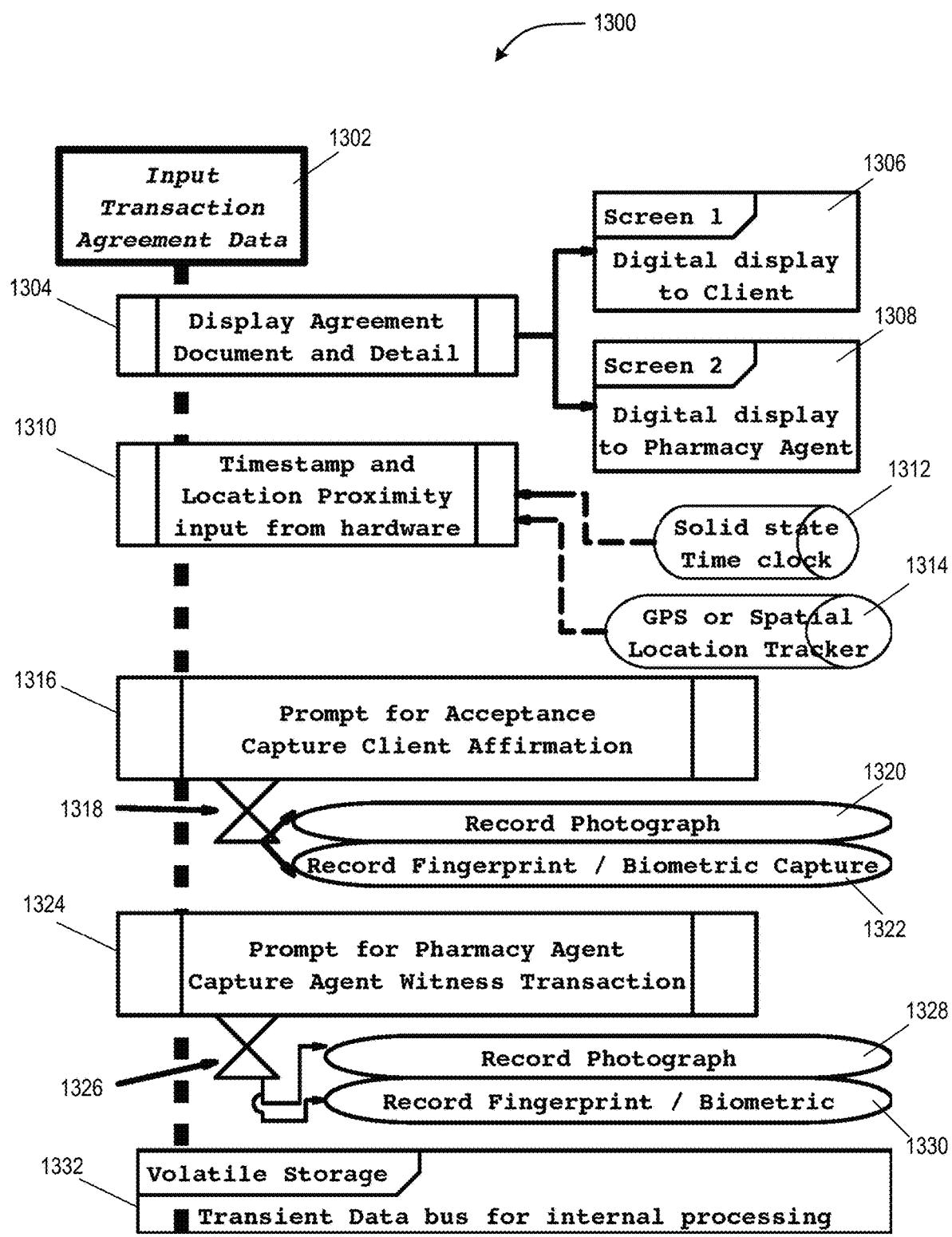
FIG. 13 is a flowchart of an example of an implementation of a data capture method for recording transactions between two parties while recording physical proximity for audit purpose in accordance with the present disclosure.

FIG. 13 is a flowchart of an example of an implementation of a data capture method 1300 for recording transactions between two parties while recording physical proximity (i.e., how physically close the two parties are to each other) for audit purpose in accordance with the present disclosure. The method 1300 starts by inputting a transaction agreement data. The data is input from an external source such as, for example, a point-of-sale operating system delivered over a communication bus in signal communication with the SBC system. In this example, the input may originate from various capture devices.

In step 1304, the SBC system displays the agreement document and details. This may be accomplished through a proprietary video controller where the output may be guaranteed with high assurance to duplicate to identical, matching, and unchanged output to at least two display screens 1306 and 1308 simultaneously. In step 1310, the method 1300 captures a timestamp and a physical proximity proof serialized into the transaction data recordings utilizing a standard solid-state or atomic clock synchronized real time mechanism 1312 and a geo-spatial data source 1314 providing an exact and identifiable location at current time and place that the biometric data was received. It is appreciated by those of ordinary skill in the art that some transactions may be enclosed or underground and, therefore, the said geo-spatial data source may be a governmental-assigned identification, serial number, or certificate in various embodiments. The SBC system then prompts 1316 the client for acceptance and captures the client's affirmation. In step 1318, the SBC system utilizes a timed control loop with software control to control the reader devices and record a photograph 1320 or a fingerprint 1322 or other biometric data. The method 1300 then prompts 1324 the service representative (i.e., the pharmacist) to record and capture an agent witness transaction. In step 1326, the SBC system utilizes a timed control loop with software control to control the reader devices and record a photograph 1328 or a fingerprint 1330 or other biometric data. The method 1300 then captures 1332 aggregated data and sends it to an audit controller for processing and encoding. The method 1300 then ends.

Figure 14:
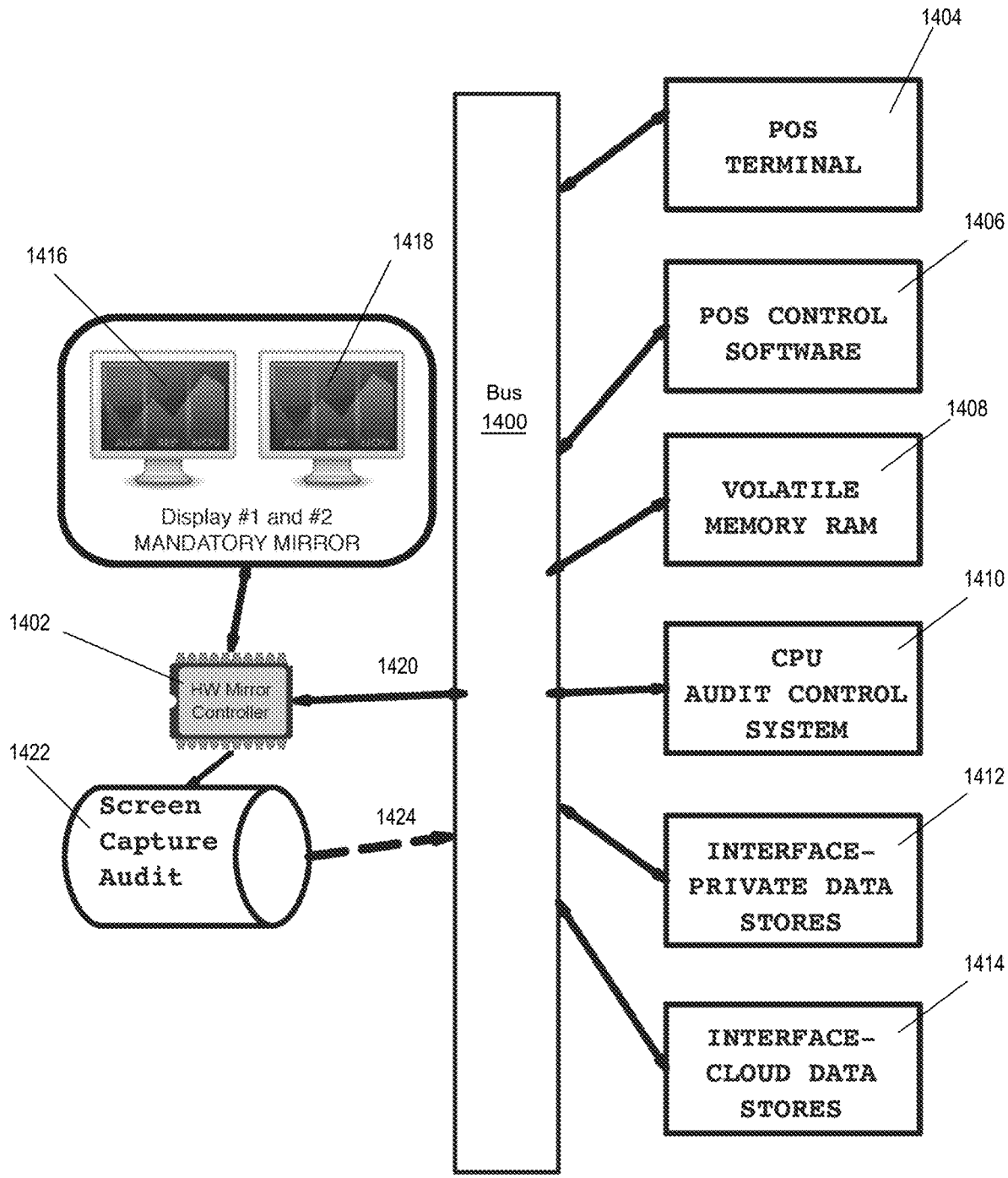
FIG. 14 is a system block diagram of an example of an implementation of the system bus, shown in FIG. 2, that provides a certified screen capture audit in accordance with the present disclosure.

FIG. 14 is a system block diagram of an example of an implementation of the system bus 1400 that provides a certified screen capture audit in accordance with the present disclosure. In this example, the bus 1400 is in signal communication with a hardware mirror controller 1402, a point-of-sale (POS) system 1403, POS control software 1406, volatile memory random access memory (RAM)

1408, CPU audit control system 1410, interface-private data stores 1412, and interface cloud data stores 1414.

In this example, the hardware mirror controller 1402 may be a proprietary video controller that is configured to guaranteed with high assurance to duplicate to provide an identical, matching, and unchanged output to at least two display screens 1416 and 1418 simultaneously. As an example, the two display screens 1416 and 1418 may be facing opposite each other with 180-degree orientation (so two people can conduct a face-to-face transaction).

In an example of operation, signal 1420 indicates data feed input delivered to the visual controller 1402 from the bus 1400. The SBC system may include a hardware screen capture device 1422 that is configured to capture recordings at a simultaneous time to be recorded for audit certification where the signal 1424 represents delivery of captured audit data returning to an audit controller system.

In this example, the volatile memory RAM 1408 is a volatile data storage mechanism available to audit controller main bus 1400 and the CPU audio control system 1410 is configured to audit control process encompassing control, serialization, data handling and encryption hardware. Furthermore, the interface-private data stores are interfaces to private electronic data stores, for example, private biometric databases for decisions and external biometric computations and the interface-cloud data stores 1414 is an interface to cloud and exported electronic data stores for permanent storage and reporting function externally.

Figure 15:
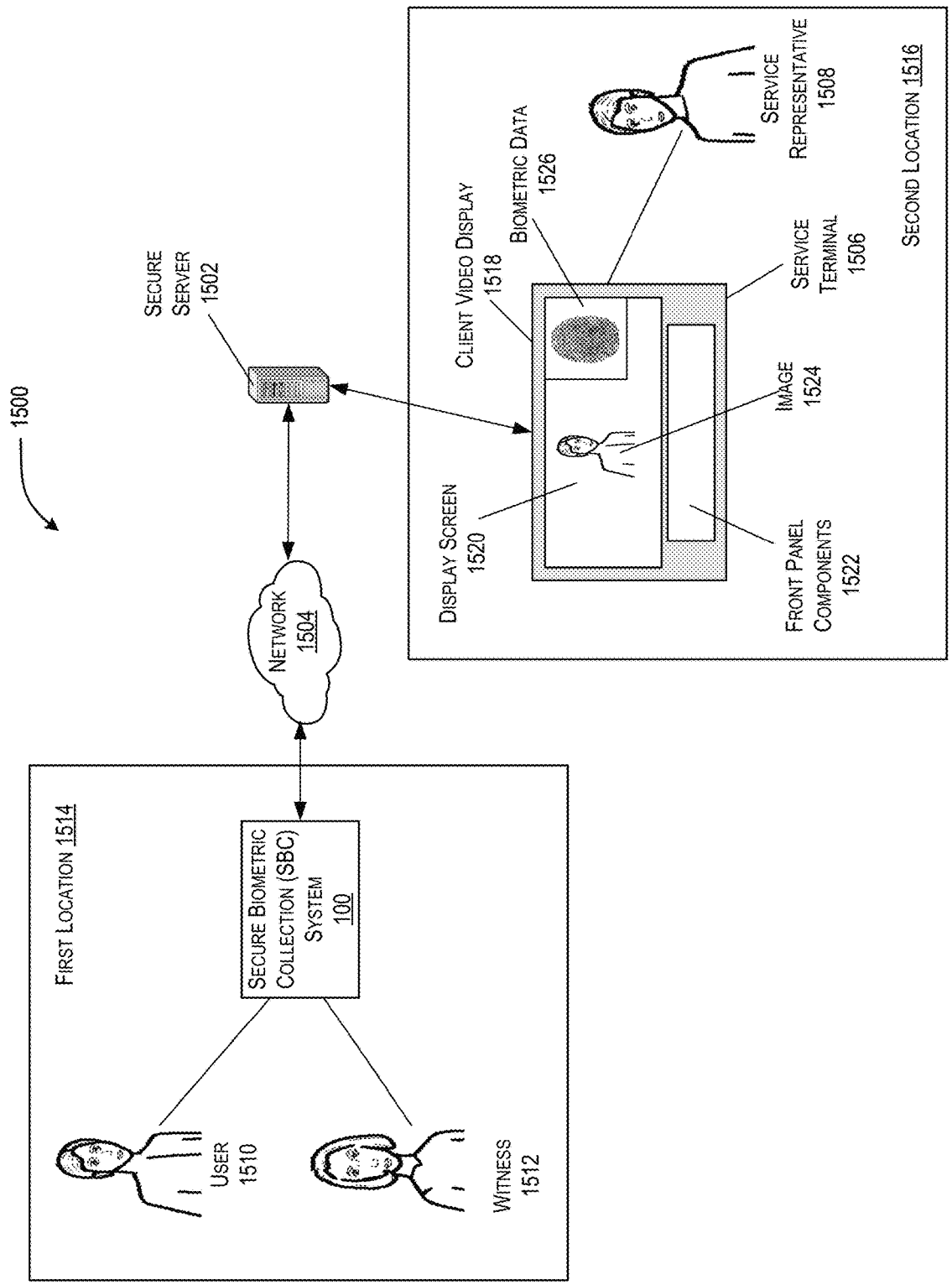
FIG. 15 is a system block diagram of an example of another implementation of the SBC system, shown in FIG. 1, within a secure network in accordance with the present disclosure.

Turning to FIG. 15, a system block diagram of an example of another implementation of the SBC system 100 within a secure network 1500 in accordance with the present disclosure. Similar to the example described in relation to FIG. 1, the secure network 1502 may include a secure server 1502 that communicates with the SBC system 100 via a network 1504. Again, the network 1506 may include one or more network such as, for example, an Ethernet network, wireless network, the Internet, a distributed blockchain network or other type of communications network. Again, in this example, the service server 1502 may include one or more servers utilized by a business or government entity to communicate and control the SBC system 100. The secure server 1502 may also communicate with a service terminal 1506 that is utilized by the business or government entity to communicate with the SBC system 100 via the secure server 1502 and network 1504. Again, the service terminal 1506 may be a computer device, such as a desktop personal computer, laptop computer, or other computer device utilized by a service representative 1508 that works for business or government entity. In this example, the secure network 1500 can also be designed as a decentralized blockchain structure.

As before, in this example, the secure network 1500 may be a secure network of a business or government entity. As an example, the government agency may be an agency that deals with the public that may be for example, taxing agencies, document processing agencies, passport services agencies, a courthouse or court related entities, recording and record keeping government departments, or other similar departments and agencies, etc. Likewise, the business entity may be a health care provider, bank, financial service provider, point-of-service vendor, or other type of business that deals with the public. In this example, the government or business entity utilizes the SBC system 100 to obtain information from a user 1510. As discussed earlier, the user 1510 maybe a buyer, customer, patient, or person seeking governmental services. The user 1510 may be a person that expects his/her personal information to be kept private. In addition to the user 1510, a witness 1512 may be present when the user 1510 interfaces with the SBC system 100. As an example, the witness 1512 may be a parent of the user 1510 if the user 1510 is a minor that is underage. In this example, the service representative 1508 may be health provider employee, government employee, or a service representative a vendor for providing services or transactions to the user 1510 that assists the user 1510 in processing his/her needs.

In this example, the SBC system 100, user 1510 and witness 1512 may be located at a first location 1514 that may be remote from a second location 1516. The service terminal 1506 and service representative 1508 are located at the second location 1516. In FIG. 1, an example was described where the user 112, witness 114, and service representative 110 may be located in the same location, however, in this example, the second location 1516 is located remote from the first location 1514. As an example, the first location 1514 may be within a specific suite of specific floor a building and the second location 1516 may be located either in another suite of the same floor the building, a different floor of the building, or in another building. Moreover, the second location 1516 may be located in another town/city or country from the first location 1514. In all of these examples, the service terminal 1506 is in signal communication with the SBC system 100 via the network 1504 and secure server 1502. Furthermore, the second location 1516 of the service terminal 1506 and service representative 1508 may be remote from the location of the secure server 1502, where the second location 1516 may be located in another town/city or country from the location of the secure server 1502 and the secure server 1502 may be in signal communication with the service terminal 1506 via another network (not shown) that again includes one or more network such as, for example, an Ethernet network, wireless network, the Internet, a distributed blockchain network or other type of communications network.

In a telemedicine type of example, the SBC system 100 may be a standalone kiosk in a medical facility at the first location 1514 and the service representative 1508 and service terminal 1506 are located a second location 1516 that may be in another building remote from the medical facility. Alternatively, in a telebanking type of example, the SBC system 100 may be a standalone kiosk in a virtual bank (i.e., a bank facility without bank tellers or personnel) at the first location 1514 and the service representative 1508 and service terminal 1506 are located a second location 1516 that may be in another building remote from the virtual bank. It is appreciated that similar examples can be described for point-of-service commercial facilities or government facilities.

In these examples, the service terminal 1506 may include a client video display 1518 having a display screen 1520 and front panel of components 1522. As a result, the service representative 1508 can see an image(s) 1524 of a photograph(s) and/or video of the user 1510 on the display screen 1520. These image(s) 1524 are recorded by the one or more cameras on the SBC system 100. Also, once the user 1510 provides their biometric data (as described earlier such as, for example, a scanned fingerprint) to the SBC system 100, the SBC system 100 may be configured to transmit that biometric data to the service terminal 1506 that displays it as biometric data 1526 on the display screen 1520. In response to this information, the service representative may provide their own biometric data (such as, for example, a scanned fingerprint) to the SBC system 100 via a biometric input device (such as, for example, a fingerprint scanner) at front panel components 1522 of the service terminal 1506.

It will be understood that various aspects or details of the disclosure may be changed without departing from the scope of the disclosure. It is not exhaustive and does not limit the claimed disclosures to the precise form disclosed. Furthermore, the foregoing description is for the purpose of illustration only, and not for the purpose of limitation. Modifications and variations are possible in light of the above description or may be acquired from practicing the disclosure. The claims and their equivalents define the scope of the disclosure. Moreover, although the techniques have been described in language specific to structural features and/or methodological acts, it is to be understood that the appended claims are not necessarily limited to the features or acts described. Rather, the features and acts are described as an example implementations of such techniques.

Conditional language such as, among others, "can," "could," "might" or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example. Conjunctive language such as the phrase "at least one of X, Y or Z," unless specifically stated otherwise, is to be understood to present that an item, term, etc. may be either X, Y, or Z, or a combination thereof.

Furthermore, the description of the different examples of implementations has been presented for purposes of illustration and description, and is not intended to be exhaustive or limited to the examples in the form disclosed. Many modifications and variations will be apparent to those of ordinary skill in the art. Further, different examples of implementations may provide different features as compared to other desirable examples. The example, or examples, selected are chosen and described in order to best explain the principles of the examples, the practical application, and to enable others of ordinary skill in the art to understand the disclosure for various examples with various modifications as are suited to the particular use contemplated.

It will also be understood that various aspects or details of the invention may be changed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

The description of the different examples of implementations has been presented for purposes of illustration and description, and is not intended to be exhaustive or limited to the examples in the form disclosed. Many modifications and variations will be apparent to those of ordinary skill in the art. Further, different examples of implementations may provide different features as compared to other desirable examples. The example, or examples, selected are chosen and described in order to best explain the principles of the examples, the practical application, and to enable others of ordinary skill in the art to understand the disclosure for various examples with various modifications as are suited to the particular use contemplated.

What is claimed is:

1. A secure biometric collection (SBC) system for collecting and recording data from a user associated with a secure transaction, the SBC system comprising:
    a storage device;
    an input device configured to receive information from the user related to the secure transaction;
    a camera configured to capture an image of the user that is stored in the storage device;
    a fingerprint scanner configured to scan a fingerprint of the user that is stored in the storage device;
    a second fingerprint scanner configured to scan a fingerprint of a witness that is stored in the storage device;
    a camera encoder configured to combine and hash the image of the user into combined data sets that are stored in the storage device;
    a fingerprint encoder configured to process the fingerprint scans of the user and witness into fingerprint template data sets and store the fingerprint template data sets in the storage device; and
    a privacy encoder configured to combine and encrypt the combined data sets and fingerprint template data sets from the storage device into encrypted data sets memorializing the secure transaction,
    wherein the SBC system is configured to produce a copy of the secure transaction that includes the encrypted data sets for the user, and wherein the storage device is configured to be purged of all the data collected from the user including the information from the user and all biometric data that includes the image of the user, fingerprint of the user, combined data sets, fingerprint template data sets, and encrypted data sets once the copy of the secure transaction is produced.

2. The SBC system of claim 1, further including a second camera, wherein the first camera is configured to capture the image of the user in a visible light range, the second camera is configured to capture a second image of the user in a non-visible light range, and the camera encoder is configured to combine and hash the image of the user in the visible light range and the image of use in the non-visible light range into the combined data sets.

3. The SBC system of claim 1, wherein the SBC system is further configured to transmit the data collected from the user including the information from the user and all biometric data that includes the image of the user, fingerprint of the user, combined data sets, fingerprint template data sets, and encrypted data sets once the copy of the secure transaction is produced to an immutable distributed ledger upon receiving the user's instruction.

4. The SBC system of claim 1, further including a second camera configured to capture an image of the witness that is stored in the storage device, wherein the camera encoder is configured to combine and hash the image of the user and the image of witness into the combined data sets.

5. The SBC system of claim 4, wherein the SBC system is located a first location and the witness is located a second location that is remote from the first location.

6. The SBC system of claim 5, wherein the second location is in a geographic location that is different from the first location.

7. The SBC system of claim 1, further including a processor, wherein the fingerprint encoder is further configured to timestamp the fingerprint scan of the user with a first timestamp and the fingerprint scan of the witness with a second timestamp, and the processor is configured to determine is the difference between the first timestamp and second timestamp is less than or equal to a predetermined time.

8. A secure biometric collection (SBC) system for collecting and recording data from a user associated with a secure transaction, the SBC system comprising:
one or more processing units; and
a computer-readable non-transitory medium having encoded thereon computer- executable instructions to cause the one or more processing units to:
receive information from the user related to the secure transaction with an input device, wherein the received information from the user is stored in a storage device,
capture an image of the user with a camera, wherein the image is stored in the storage device,
scan a fingerprint of the user with a fingerprint scanner, wherein the fingerprint of the user is stored in the storage device,
scan a fingerprint of a witness with a second fingerprint scanner;
combine and hash the image of the user into combined data sets that are stored in the storage device,
process the fingerprint scan of the user and fingerprint scan of the witness into fingerprint template data sets that are stored in the storage device,
combine and encrypt the combined data sets and fingerprint template data sets from the storage device into encrypted data sets memorializing the secure transaction,
produce a copy of the secure transaction that includes the encrypted data sets for the user, and
purge all the data collected from the user including the information from the user and all biometric data that includes the image of the user, fingerprint of the user, combined data sets, fingerprint template data sets, and encrypted data sets once the copy of the secure transaction is produced.

9. The SBC system of claim 8, further including capturing a second image of the user with a second camera, wherein the first camera is configured to capture the image of the user in a visible light range and the second camera is configured to capture a second image of the user in a non-visible light range, and the computer-executable instructions to cause the one or more processing units to combine and hash the visible image of the user and the non-visible image of the user into combined data sets.

10. The SBC system of claim 8, wherein the SBC system transmits the data collected from the user including the information from the user and all biometric data that includes the image of the user, fingerprint of the user, combined data sets, fingerprint template data sets, and encrypted data sets once the copy of the secure transaction is produced to an immutable distributed ledger upon receiving the user's instruction.

11. The SBC system of claim 8, wherein the computer-executable instructions cause the one or more processing units to scan a fingerprint of a witness with a second fingerprint scanner and process the fingerprint scan of the user and fingerprint scan of the witness into the fingerprint template data sets.

12. The SBC system of claim 11, wherein the computer-executable instructions are configured to further cause the one or more processing units to capture an image of the witness with a second camera, wherein the image of the witness is stored in the storage device, and combine and hash the image of the user and the image of the witness into combined data sets.

13. The SBC system of claim 12, wherein the SBC system is located a first location and the witness is located a second location that is remote from the first location.

14. The SBC system of claim 13, wherein the second location is in a geographic location that is different from the first location.

15. The SBC system of claim 11, wherein the computer-executable instructions are configured to further cause the one or more processing units to timestamp the fingerprint scan of the user with a first timestamp and the fingerprint scan of the witness with a second timestamp, and determine is the difference between the first timestamp and second timestamp is less than or equal to a predetermined time.

16. A method for collecting and recording data from a user associated with a secure transaction with a secure biometric collection (SBC) system, the method comprising:
receiving information from the user related to the secure transaction with an input device;
storing the received information from the user in a storage device;
capturing an image of the user with a camera;
storing the image in the storage device; scanning a fingerprint of the user with a fingerprint scanner;
scanning a fingerprint of a witness with a second fingerprint scanner;
storing the fingerprint of the user in the storage device;
combining and hashing the image of the user into combined data sets;
storing the combined data sets in the storage device;
processing the fingerprint scan of the user and the fingerprint scan of the witness into fingerprint template data sets;
storing the fingerprint template data sets in the storage device;
combining and encrypting the combined data sets and fingerprint template data sets from the storage device into encrypted data sets memorializing the secure transaction;
producing a copy of the secure transaction that includes the encrypted data sets for the user; and
purging all the data collected from the user including the information from the user and all biometric data that includes the image of the user, fingerprint of the user, combined data sets, fingerprint template data sets, and encrypted data sets upon production of the copy of the secure transaction.

17. The method of claim 16, further comprising transmitting the data collected from the user including the information from the user and all biometric data that includes the image of the user, fingerprint of the user, combined data sets, fingerprint template data sets, and encrypted data sets once the copy of the secure transaction is produced to an immutable distributed ledger upon receiving the user's instruction.

18. The method of claim 16, further including capturing a second image of the user with a second camera, wherein the first camera is configured to capture the image of the user in a visible light range and the second camera is configured to capture a second image of the user in a non-visible light range, and wherein combining and hashing the image of the user into combined data sets includes combining and hashing the visible light image of the user and the non-visible light image of the user into combined data sets.

19. The method of claim 16, wherein the SBC system is located at a first location and the witness is located at a second location that is remote from the first location.

\* \* \* \* \*